US012592323B2

(12) United States Patent
Morse et al.

(10) Patent No.: US 12,592,323 B2
(45) Date of Patent: \*Mar. 31, 2026

(54) TARGETED GENERATION OF MESSAGES FOR DIGITAL THERAPEUTICS USING GENERATIVE TRANSFORMER MODELS

(71) Applicant: Click Therapeutics, Inc., New York, NY (US)

(72) Inventors: William Morse, New York, NY (US); Qingzhe Li, Warren Township, NJ (US)

(73) Assignee: Click Therapeutics, Inc., New York, NY (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/747,260

(22) Filed: Jun. 18, 2024

(65) Prior Publication Data

US 2025/0111954 A1 Apr. 3, 2025

Related U.S. Application Data

(63) Continuation of application No. 18/374,483, filed on Sep. 28, 2023, now Pat. No. 12,057,238.

(51) Int. Cl.
*G16H 80/00* (2018.01)
*G16H 20/70* (2018.01)
*H04W 4/12* (2009.01)

(52) U.S. Cl.
CPC .............. *G16H 80/00* (2018.01); *G16H 20/70* (2018.01); *H04W 4/12* (2013.01)

(58) Field of Classification Search
CPC ......... G16H 80/00; G16H 20/70; H04W 4/12; H04W 4/14
See application file for complete search history.

(56) References Cited

U.S. PATENT DOCUMENTS 10,943,407 B1 \* 3/2021 Morgan ................. G16H 15/00
11,516,158 B1 11/2022 Luzhnica et al.
(Continued)

FOREIGN PATENT DOCUMENTS

WO WO-2004053770 A2 \* 6/2004 ............. G16H 70/20

OTHER PUBLICATIONS

Andrews et al.; Acceptability of a Pain History Assessment and Education Chatbot (Dolores) Across Age Groups in Populations With Chronic Pain: Development and Pilot Testing; JMIR Form Res 2023;7:e47267 (Year: 2023).\*

(Continued)

*Primary Examiner* — Hiep V Nguyen
(74) *Attorney, Agent, or Firm* — MORRISON & FOERSTER LLP

(57) ABSTRACT

Aspects of the present disclosure are directed to systems, methods, and computer readable media for generating messages targeted to address conditions in users. A computing system may identify (i) a condition of a user to be addressed and (ii) one or more parameters defining messages to be presented via an application towards achieving an endpoint associated with the condition for the user. The computing system may generate a prompt using the condition and the one or more parameters in accordance with a template. The computing system may apply the prompt to a generative model to output a message identifying at least one activity toward achieving the endpoint. The generative model may be trained using a corpus. The computing system may provide, the message for presentation to prompt the user to perform the activity via the application towards achieving the endpoint to address the condition.

24 Claims, 7 Drawing Sheets

(56)          References Cited

U.S. PATENT DOCUMENTS

| | | |
|---|---|---|
| 2017/0235885 A1 | 8/2017 | Cox |
| 2019/0103192 A1* | 4/2019 | Bent ..................... G16H 10/60 |
| 2020/0004583 A1 | 1/2020 | Kelly et al. |

OTHER PUBLICATIONS

Extended European Search Report on EP Application No. 24151482.7 dated Jul. 9, 2024.

Non-Final Office Action on U.S. Appl. No. 18/374,483 dated Dec. 4, 2023.

Notice of Allowance on U.S. Appl. No. 18/374,483 dated Mar. 29, 2024.

Ricci, Laetitia; Flare-IB D: development and validation of a questionnaire based on patients' messages on an internet forum for early detection of flare in inflammatory bowel disease: study protocol; BMJ Open 10.7: e037211. BMJ Publishing Group LTD. (2020) (Year: 2020).

\* cited by examiner

TARGETED GENERATION OF MESSAGES FOR DIGITAL THERAPEUTICS USING GENERATIVE TRANSFORMER MODELS

CROSS REFERENCES TO RELATED APPLICATIONS

This application claims priority under 35 U.S.C. § 120 as a continuation of U.S. patent application Ser. No. 18/374,483, titled "Targeted Generation of Messages for Digital Therapeutics Using Generative Transformer Models," filed Sep. 28, 2023, which is incorporated herein by reference in its entirety for all purposes.

BACKGROUND

In a networked environment, a server can transmit a message to an end user device to provide various information to the end user. This message may have been manually created by a content provider associated with the server, and may be part of a pre-defined, fixed, and linear sequence of messages selected by the server for the end user using various criterion. This predefined sequence may be unsuitable for certain applications. For example, in the context of digital therapeutics, the predefined sequence of messages may not account for changes to the end user's state, such as improvement or degradation of the end user's condition or adherence to the digital therapeutic.

Since the sequence is selected and set at the beginning of the end user's therapy regimen, the sequence may also not factor in feedback from the user in a flexible and robust manner. The static nature of the sequencing and the content within the messages themselves may be especially problematic when the message contains interactive elements with which the end user is to interact as part of the therapy regimen. Furthermore, as the content for these messages may have been individually and manually created, the creation of the content may be resource intensive. There may be also a lack of scalability to a broader audience and at the same time insufficient specificity to a particular end user's condition. The lack of flexibility, scalability, and specificity in the manual creation of messages and rules to select messages can result in wasted consumption of computing resources (e.g., processor and memory) and network bandwidth from providing ineffective messages. From a human-computer interaction (HCI) perspective, these issues may potentially lead to lack of user interaction and lower adherence.

SUMMARY

To address these and other challenges, a messaging service can leverage a generative artificial intelligence (AI) (e.g., generative transformer models) to produce messages for end-users targeted at addressing their specific conditions for digital therapeutic applications. The message created using such generative transformer models (e.g., large language models or text-to-image models) may include content to be presented via the end-user's device, with the aim of preventing, alleviating, or treating conditions of the end-user. The generative transformer model can be trained using general and domain-specific corpora (e.g., text or text associated with other modalities of content, including images, videos, audio, or multimedia content) as well as pre-built messages to generate messages targeted at the end user's specific condition and rules to select from the pre-built messages. In addition, using feedback, the model may be further fine-tuned to output content for messages that factor in the specific user's behavior, preferences, and other characteristics in furtherance of the digital therapeutic treatment regimen.

In generating the messages, the service can generate a prompt in accordance with a template using information associated with a particular user and parameters defining the generation of the content. The information can include, for example, the user's condition, state, behavior, preferences, and responses to previous messages, among others. The message definition parameters can identify, for instance, time of day at which to present the message, difficulty setting of messages, and previously generated or provided messages, among others. The template for the prompt can include a set of strings (e.g., words, phrases, and other text) and placeholders for the insertion of the information about the user and the message definition parameters. With the generation, the service can apply the prompt to the generative transformer model to output content for the message. The message can include, for example, content forming a notification for the end user in connection with the treatment regime for the condition or an instruction for the end user to perform a specified activity towards achieving an endpoint in connection with addressing the condition or a psycho-education lesson providing clinical training to the end user. The message can also include a time at which to send or present the message.

With the output from the generative transformer model, the service can send the message containing the content output by the generative transformer model for presentation on the end-user device. The message can be sent or presented on the end-user device at the time defined by the output content. An application running on the end user device can present the content of the message. Upon presentation via the end-user device, the message can direct the end user to perform an activity in furtherance of the digital therapeutic therapy regimen. The application on the end user device can monitor for interactions by the end-user with the message or the application itself. The interaction can include, for example, an indication that the specified activity has been performed or an input of the user's reaction to the presentation of the message, among other responses. Using the detected interactions, the application can generate and send a response to provide to the messaging service.

Upon receipt, the message service can use the response from the end user device to update the generative transformer model itself. The message service can parse the response of the end user device to generate feedback data. The feedback data may include information, such as the content that was included in the message provided to the user and an indication whether the user performed the activities specified in the content of the message. The feedback data can be used to update the generative transformer model itself. For instance, the messaging service can use the feedback data to calculate a loss metric as a function of the feedback data, and then use the loss metric to update the weights in the generative transformer model. The feedback data may also be used to generate subsequent prompts when creating messages for the end user using the generative transformer model. For example, the service can add at least a portion of the feedback data as part of the user information or the message generation parameters when generating the prompt. The service can combine the feedback data from any number of previously presented messages when creating the prompt to input into the generative transformer model.

In this manner, the messaging service may iteratively and continuously factor in feedback from presentations of messages to the end user when generating subsequent content using the generative transformer model. Relative to the predefined, fixed sequence of content as in other approaches, the incorporation of the feedback data by the service can allow for new generation of content more pertinent to the end user's changing state and preferences. In the context of digital therapeutics, the new generation of content may account for changes to the end user's state, such as improvement or degradation of the end user's condition or progression through the therapy regimen.

Furthermore, with the use of the generative transformer model, the service can generate content specifically targeting end-users' condition and state in a flexible manner and can scale the individualization of content to a large audience. The enablement of flexibility, scalability, and specificity can optimize or reduce consumption of computing resources (e.g., processor and memory) and network bandwidth that would have been otherwise wasted from providing ineffective content. From a human-computer interaction (HCI) perspective, the content generated by leveraging of the generative transformer model can yield higher quality of interactions by the user with the application. In addition, the increase in engagement can result in higher levels of adherence of the user with the therapy regimen, thereby leading to a greater likelihood in preventing, alleviating, or treating conditions of the end-user.

Aspects of the present disclosure are directed to systems, methods, and computer readable media for providing messages targeted to address conditions in users. A computing system may identify (i) a condition of a user to be addressed and (ii) one or more parameters defining messages to be presented via an application towards achieving an endpoint associated with the condition for the user. The computing system may generate a prompt using the condition and one or more parameters in accordance with a template. The computing system may apply the prompt to a generative model comprising a plurality of weights to output a message identifying at least one activity toward achieving the endpoint. The generative model may be established by identifying a plurality of corpora, each corpus of the plurality of corpora comprising a respective first dataset; applying at least a portion of the respective first dataset of each of the plurality of corpora to the generative model to generate a respective second dataset; comparing a first distribution of tokens in at least the portion of the respective first dataset and a second distribution of tokens in the respective second dataset for each of the plurality of corpora; and updating one or more of the plurality of weights in the generative model based on the comparison. The computing system may provide the message for presentation to prompt the user to perform the activity via the application towards achieving the endpoint to address the condition.

In some embodiments, the computing system may receive a response identifying performance of the activity by the user via the application responsive to the presentation of the message. The computing system may determine, based on the response, one or more second parameters to define the messages to be presented for the user.

In some embodiments, the computing system may retrieve, from a database, a plurality of candidate messages based on the endpoint towards which to achieve for the user to address the condition. In some embodiments, the computing system may identify one or more parameters to include the plurality of candidate messages to define the messages to be presented. In some embodiments, the computing system may apply the prompt to the generative model to select the message from the plurality of candidate messages. In some embodiments, the generative model may be trained using a set of rules defining selection from a plurality of candidate messages based on at least one of: (i) user behavior, (ii) user preferences, or (iii) user profile information.

In some embodiments, the computing system may apply the prompt to the generative model to generate the message. At least one of the plurality of corpora used to train the generative model may include a plurality of datasets associated with the condition to be addressed. In some embodiments, the computing system may update the generative model for the user using a response identifying performance of the activity by the user via the application responsive to the presentation of the message. In some embodiments, the computing system may apply the prompt comprising a plurality of text strings to the generative model to generate the message to include visual content. At least one of the plurality of corpora used to train the generative model may include textual data and visual data.

In some embodiments, the computing system may apply a second prompt to the generative model to output a second message for a lesson identifying information for the user towards achieving the endpoint. In some embodiments, the computing system using a tokenizer may convert a plurality of strings of the prompt to a plurality of tokens to be used to generate the message. In some embodiments, the tokenizer may be trained using a second corpus of textual data associated with a plurality of conditions to be addressed and a plurality of endpoints towards achieving for at least one of the plurality of conditions. In some embodiments, the user may be on a medication to address the condition, in partial concurrence with a session in which the message is provided. In some embodiments, the computing system may determine a time at which to present the message to the user, using a delivery model for the user. In some embodiments, the message may include at least one of: a short messaging service (SMS) message, a multimedia messaging service (MMS) message, or an in-app message.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

For purposes of reading the description of the various embodiments below, the following enumeration of the sections of the specification and their respective contents may be helpful:

Section A describes systems and methods for providing messages targeted to address conditions in users; and Section B describes a network and computing environment which may be useful for practicing embodiments described herein.

Figure 1:
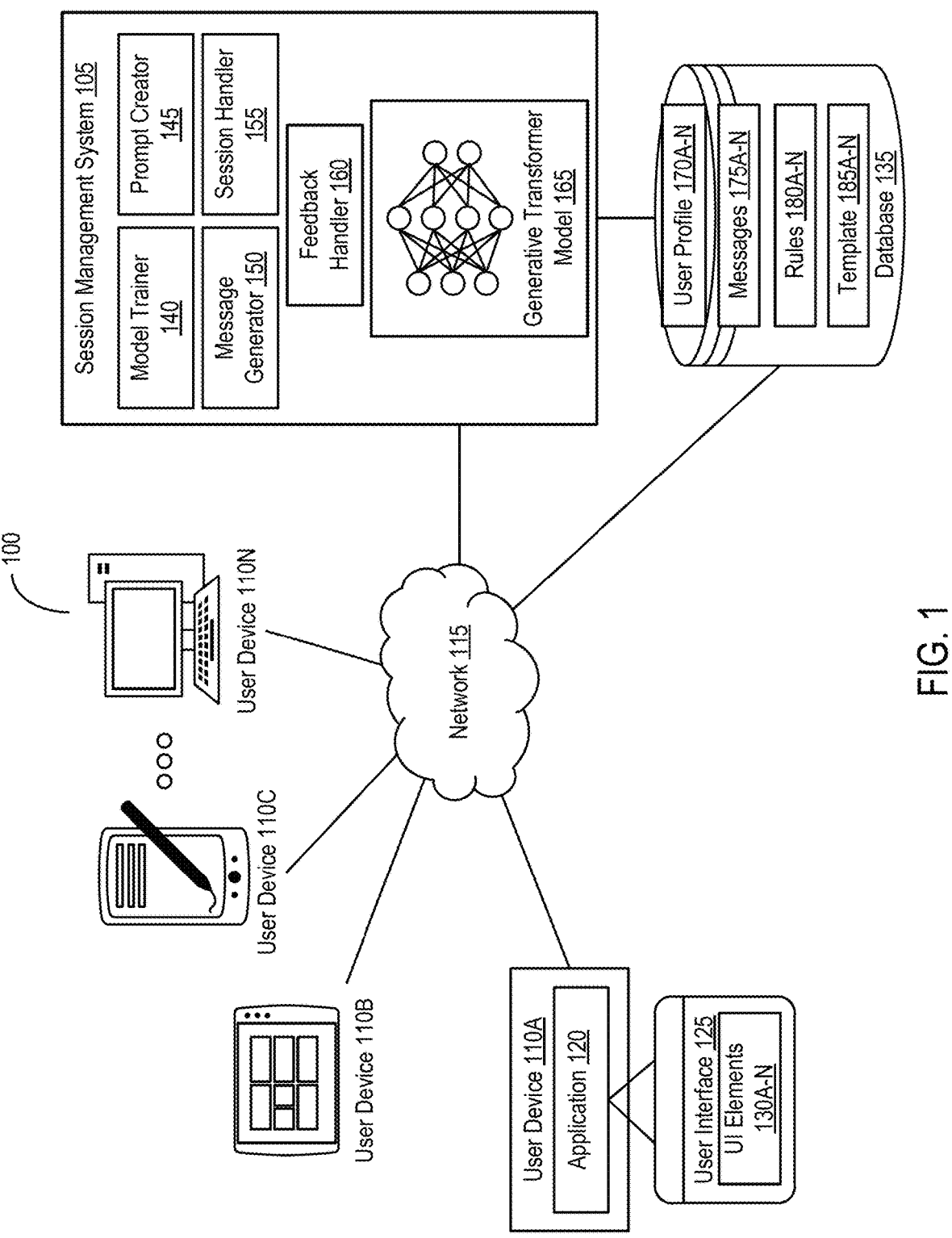
FIG. 1 depicts a block diagram of a system for generating messages targeted at addressing conditions in users in accordance with an illustrative embodiment.

A. Systems and Methods for Providing Messages Targeted to Address Conditions in Users Referring now to FIG. 1, depicted is a block diagram of a system 100 for generating messages targeted at addressing conditions in users. In an overview, the system 100 may include at least one session management service 105 and a set of user devices 110A-N (hereinafter generally referred to as user devices 110), communicatively coupled with one another via at least one network 115. At least one of the user devices 110 (e.g., the first user device 110A as depicted) may include at least one application 120. The application 120 may include or provide at least one user interface 125 with one or more user interface (UI) elements 130A-N (hereinafter generally referred to as UI elements 130). The session management system 105 may include at least one model trainer 140, at least one prompt creator 145, at least one message generator 150, at least one session handler 155, at least one feedback handler 160, and at least one generative transformer model 165, among others. The session management system 105 may include or have access to at least one database 135. The database 135 may store, maintain, or otherwise include one or more user profiles 170A-N (hereinafter generally referred to as user profiles 170), one or more messages 175A-N (hereinafter generally referred to as messages 175), one or more rules 180 A-N (hereinafter generally referred to as rules 180), and one or more templates 185A-N (hereinafter generally templates 185), among others. The functionalities of the application 120 on the user device 110 may be performed in part on the session management system 105, and vice-versa.

In further detail, the session management system 105 (sometimes herein generally referred to as a messaging service) may be any computing device comprising one or more processors coupled with memory and software and capable of performing the various processes and tasks described herein. The session management system 105 may be in communication with the one or more user devices 110 and the database 175 via the network 115. The session management service 105 may be situated, located, or otherwise associated with at least one computer system. The computer system may correspond to a data center, a branch office, or a site at which one or more computers corresponding to the session management system 105 are situated.

Within the session management system 105, the model trainer 140 may train, improve, or update the generative transformer model 165 related to a session initiated by a user of the application 120. The prompt creator 145 may generate a prompt using a condition and one or more parameters derived from one or more templates 185. The message generator 150 may generate messages 175 by feeding prompts into the generative transformer model 165. The session handler 155 may provide messages 175 related to a session initiated by a user of the application 120 on respective user devices 110. The feedback handler 160 may generate feedback using responses from the user device 110 to update the generative transformer model 165.

The generative transformer model 165 may receive inputs in the form of a set of strings (e.g., from a text input) to output content in one or more modalities (e.g., in the form of text strings, audio content, images, video, or multimedia content). The generative transformer model 165 may be a machine learning model in accordance with a transformer model (e.g., generative pre-trained model or bidirectional encoder representations from transformers). The generative transformer model 165 can be a large language model (LLM), a text-to-image model, a text-to-audio model, or a text-to-video model, among others. In some embodiments, the generative transformer model 165 can be a part of the session management system 105 (e.g., as depicted). In some embodiments, the generative transformer model 165 can be part of a server separate from and in communication with the session management system 105 via the network 115.

The generative transformer model 165 can include a set of weights arranged across a set of layers in accordance with the transformer architecture. Under the architecture, the generative transformer model 165 can include at least one tokenization layer (sometimes referred to herein as a tokenizer), at least one input embedding layer, at least one position encoder, at least one encoder stack, at least one decoder stack, and at least one output layer, among others, interconnected with one another (e.g., via forward, backward, or skip connections). In some embodiments, the generative transformer layer 165 can lack the encoder stack (e.g., for an decoder-only architecture) or the decoder stack (e.g., for a encoder-only model architecture). The tokenization layer can convert raw input in the form of a set of strings into a corresponding set of word vectors (also referred to herein as tokens or vectors) in an n-dimensional feature space. The input embedding layer can generate a set of embeddings using the set of word vectors. Each embedding can be a lower dimensional representation of a corresponding word vector and can capture the semantic and syntactic information of the string associated with the word vector. The position encoder can generate positional encodings for each input embedding as a function of a position of the corresponding word vector or by extension the string within the input set of strings.

Continuing on, in the generative transformer model 165, an encoder stack can include a set of encoders. Each encoder can include at least one attention layer and at least one feed-forward layer, among others. The attention layer (e.g., a multi-head self-attention layer) can calculate an attention score for each input embedding to indicate a degree of attention the embedding is to place focus and generate a weighted sum of the set of input embeddings. The feed-forward layer can apply a linear transformation with a non-linear activation (e.g., a rectified linear unit (ReLU)) to the output of the attention layer. The output can be fed into another encoder in the encoder stack in the generative transformer layer 165. When the encoder is the terminal encoder in the encoder stack, the output can be fed to the decoder stack.

The decoder stack can include at least one attention layer, at least one encoder-decoder attention layer, and at least one feed-forward layer, among others. In the decoder stack, the attention layer (e.g., a multi-head self-attention layer) can calculate an attention score for each output embedding (e.g., embeddings generated from a target or expected output). The encoder-decoder attention layer can combine inputs from the attention layer in the decoder stack and the output from one of the encoders in the encoder stack and can calculate an attention score from the combined input. The feed-forward layer can apply a linear transformation with a non-linear activation (e.g., a rectified linear unit (ReLU)) to the output of the encoder-decoder attention layer. The output of the decoder can be fed to another decoder in the decoder stack. When the decoder is the terminal decoder in the decoder stack, the output can be fed to the output layer.

The output layer of the generative transformer model 165 can include at least one linear layer and at least one activation layer, among others. The linear layer can be a fully connected layer to perform a linear transformation on the output from the decoder stack to calculate token scores. The activation layer can apply an activation function (e.g., a softmax, sigmoid, or rectified linear unit) to the output of the linear function to convert the token scores into probabilities (or distributions). The probability may represent a likelihood of occurrence for an output token, given an input token. The output layer can use the probabilities to select an output token (e.g., at least a portion of output text, image, audio, video, or multimedia content with the highest probability). Repeating this over the set of input tokens, the resultant set of output tokens can be used to form the output of the overall generative transformer model 165. While described primarily herein in terms of transformer models, the session management system 105 can use other machine learning models to generate and output content.

The user device 110 (sometimes herein referred to as an end user computing device) may be any computing device comprising one or more processors coupled with memory and software and capable of performing the various processes and tasks described herein. The user device 110 may be in communication with the session management system 105 and the database 135 via the network 115. The user device 110 may be a smartphone, other mobile phone, tablet computer, wearable computing device (e.g., smart watch, eyeglasses), or laptop computer. The user device 110 may be used to access the application 120. In some embodiments, the application 120 may be downloaded and installed on the user device 110 (e.g., via a digital distribution platform). In some embodiments, the application 120 may be a web application with resources accessible via the network 115.

The application 120 executing on the user device 110 may be a digital therapeutics application and may provide a session (sometimes referred to herein as a therapy session) to address at least one condition of the user. The condition of the user may include, for example, a chronic pain (e.g., associated with or include arthritis, migraine, fibromyalgia, back pain, Lyme disease, endometriosis, repetitive stress injuries, irritable bowel syndrome, inflammatory bowel disease, and cancer pain), a skin pathology (e.g., atopic dermatitis, psoriasis, dermatillomania, and eczema), a cognitive impairment (e.g., mild cognitive impairment (MCI), Alzheimer's, multiple sclerosis, and schizophrenia), a mental health conditions (e.g., an affective disorder, bipolar disorder, obsessive-compulsive disorder, borderline personality disorder, and attention deficit/hyperactivity disorder), a substance use disorder (e.g., opioid use disorder, alcohol use disorder, tobacco use disorder, or hallucinogen disorder), and other ailments (e.g., narcolepsy and oncology), among others.

The user may be at least partially concurrently taking medication to address the condition, while being provided sessions through application 120. For instance, if the medication is for pain, the user may be taking acetaminophen, a nonsteroidal anti-inflammatory composition, an antidepressant, an anticonvulsant, or other composition, among others. For skin pathologies, the user may be taking a steroid, antihistamine, or topic antiseptic, among others. For cognitive impairments, the user may be taking cholinesterase inhibitors or memantine, among others. For narcolepsy, the user may be taking a stimulant or antidepressant, among others. The user of the application 120 may also participate in other psychotherapies for these conditions.

The application 120 can include, present, or otherwise provide a user interface 145 including the one or more user interface elements 130A-N (hereinafter generally referred to as UI elements 130) to a user of the user device 110 in accordance with a configuration on the application 120. The UI elements 130 may correspond to visual components of the user interface 125, such as a command button, a text box, a check box, a radio button, a menu item, and a slider, among others. In some embodiments, the application 120 may be a digital therapeutics application and may provide a session (sometimes referred to herein as a therapy session) via the user interface 145 towards achieving an endpoint of the user (sometimes herein referred to as a patient, person, or subject). An endpoint can be, for example, a completion of the session, a physical or mental goal of a user, a completion of a medication regimen, or an endpoint indicated by a doctor or a user.

The database 135 may store and maintain various resources and data associated with the session management system 105 and the application 120. The database 135 may include a database management system (DBMS) to arrange and organize the data maintained thereon, as the user profiles 170, the messages 175, the rules 180, and the templates 185, among others. The database 135 may be in communication with the session management system 105 and the one or more user devices 110 via the network 115. While running various operations, the session management system 105 and the application 120 may access the database 135 to retrieve identified data therefrom. The session management system 105 and the application 120 may also write data onto the database 135 from running such operations.

On the database 135, each user profile 170 (sometimes herein referred to as a user account, user information, or subject profile) can store and maintain information related to a user of the application 120 through user device 110. Each user profile 170 may be associated with or correspond to a respective user of the application 120. The user profile 170 may identify various information about the user, such as a user identifier, the condition to be addressed, information on sessions conducted by the user (e.g., activities or lessons completed), message preferences, user trait information, and a state of progress (e.g., completion of endpoints) in addressing the condition, among others. The information on a session may include various parameters of previous sessions performed by the user and may be initially null. The message preferences can include treatment preferences and user input preferences, such as types of messages or timing of messages preferred. The message preferences can also include preferences determined by the session management system 105, such as a type of message the user may respond to. The progress may initially be set to a start value (e.g., null or "0") and may correspond to alleviation, relief, or treatment of the condition. The user profile 170 may be continuously updated by the application 120 and the session management system 105.

In some embodiments, the user profile 170 may identify or include information on a treatment regimen undertaken by the user, such as a type of treatment (e.g., therapy, pharmaceutical, or psychotherapy), duration (e.g., days, weeks, or years), and frequency (e.g., daily, weekly, quarterly, annually), among others. The user profile 170 can include at least one activity log of messages provided to the user, interactions by the user identifying performance of the specific user, and responses from the user device 110 associated with the user, among others. The user profile 170 may be stored and maintained in the database 135 using one or more files (e.g., extensible markup language (XML), comma-separated values (CSV) delimited text files, or a structured query language (SQL) file). The user profile 170 may be iteratively updated as the user performs additional sessions or responds to additional messages 175.

Each message 175 may identify or include information to be presented via the user device 110. The message 175 may be in any format, such as a short message/messaging service (SMS), a multimedia messaging service (MMS), or as an instruction to display via the UI elements 130 of the user interface 125 through the application 120 (e.g., an in-application message), among others. The information of the message 175 may include reminders to perform a task of the session. The message 175 may be delivered periodically, such as daily, weekly, or monthly, among others. The message 175 may be derived from a library of pre-generated psychotherapy messages or a library of pre-generated engagement (reminder) messages. The message 175 may include reminders for the subject to complete the therapy sessions, to take medication, or to complete a task of the regimen. The message 175 may be personalized based on the user's activity, adherence, or performance in relation to the regimen. The message 175 may also include a mechanism for responding, such as a link, chat box, or indication to respond to the message. For example, when presented through the application 120, the content for the message 175 can be presented through one or more UI elements 130 with which the user can interact.

The message 175 may include an activity for the user to perform or a lesson for the user to engage with. A message 175 identifying an activity to be performed can identify one or more interactive elements with which the user can interact to indicate or record performance of the activity through the application 120 towards achieving an endpoint. A message 175 for a lesson can include information that the user is to consume (e.g., by viewing or reading) towards achieving an endpoint. The information can include digital therapeutic content to be presented to the user. For instance, the message 175 can include educational content explaining the user the relationship between exercise and mental health. In some embodiments, the information for the message 175 can identify a set of activities towards achieving the endpoint. In some embodiments, the message 175 for the lesson can include interactive elements with which the user can interact to navigate through the information or to perform the activities. In some embodiments, the message 175 for the lesson can lack interactive elements to indicate performance of the activity through the application 120.

The message 175 may include content in any modality, such as text, image, audio, video, or multimedia content, among others, or any combination thereof. The message 175 can be stored and maintained in the database 135 using one or more file. For instance, for text, the message 175 can be stored as text files (TXT), rich text files (RTF), extensible markup language (XML), and hypertext markup language (HTTP), among others. For an image, the message 175 may be stored as a joint photographic experts' group (JPEG) format, a portable network graphics (PNG) format, a graphics interchange format (GIF), or scalable vector graphics (SVG), among others. For audio, the message 175 can be stored as a waveform audio file (WAV), motion pictures expert group formats (e.g., MP3 and MP4), and Ogg Vorbis (OGG), among others. For video, the message 175 can be stored as a motion pictures expert group formats (e.g., MP3 and MP4), QuickTime movie (MOV), and Windows Movie Video (WMV), among others. For multimedia content, the message 175 can be an audio video interleave (AVI), motion pictures expert group formats (e.g., MP3 and MP4), Quick-Time movie (MOV), and Windows Movie Video (WMV), among others. The message 175 can be associated with metadata, such as a description of the content or information included in the message 175.

Each rule 180 can specify, identify, or otherwise define logic to select or identify one of the messages 175 for the presentation to the user. The logic specified by the rule 180 may be derived from user behavior, user preferences, or profile information for a given user, among others. For example, the rule 180 can define selection of a particular message 175 to a user with schizophrenia, when the time is between 8:00 a.m. and 10:00 a.m. The user behavior may include, for example, a type of activities performed by the user as identified in the activity log associated with the user as identified in the user profile 170. The user preference may correspond to types of messages preferred by the user as identified in the user profile 170. The profile information may include other data points about the user used to select the message 175, such as a progress of treatment, a difficulty level, or a stage on the path to achieving an endpoint, among others. The rule 180 may be used by the session management service 105 to select messages 175 to provide to end users at user devices 110. The rule 180 can be used to provide the generative transformer model 165 with base knowledge of the domain in which it is used. The base knowledge of the domain can, for example, correspond to information for a particular digital therapeutics treatment, such as information about the application 120 and the condition to be addressed through the application 120, including chronic pain, skin pathology, cognitive impairment, mental health conditions, or substance use disorder, among others. The rule 180 may be used to train or fine-tune the generative transformer model 165 in outputting content for messages. The rule 180 may be derived and verified from clinical trials to provide a variety of circumstances for the generative transformer model 165 to generate a desired message.

Each template 185 can specify, identify, or otherwise define a set of strings with one or more placeholders to be inserted using inputs among the set of strings. The template 185 can be used to write, create, or produce prompts to be applied to the generative transformer model 165 to output. The placeholders can define or identify a contribution region within each template 185. Each contribution region may be filled with the inputs for a given user, depending on their respective condition, and parameters defining the messages to be presented to the end users. As an example, a template 185 may state "Given a smoker _ years old. He has been smoking for _ years. He finished lessons _. He has only smoked _ during the past 3 days. Can you help me _ message to encourage him finish the next lesson _ and try not smoking today." The template 185 can be stored and maintained in the database 135 using one or more files (e.g., text files (TXT), rich text files (RTF), extensible markup language (XML), comma-separated values (CSV) delimited text files, or a structured query language (SQL) file).

Figure 2:
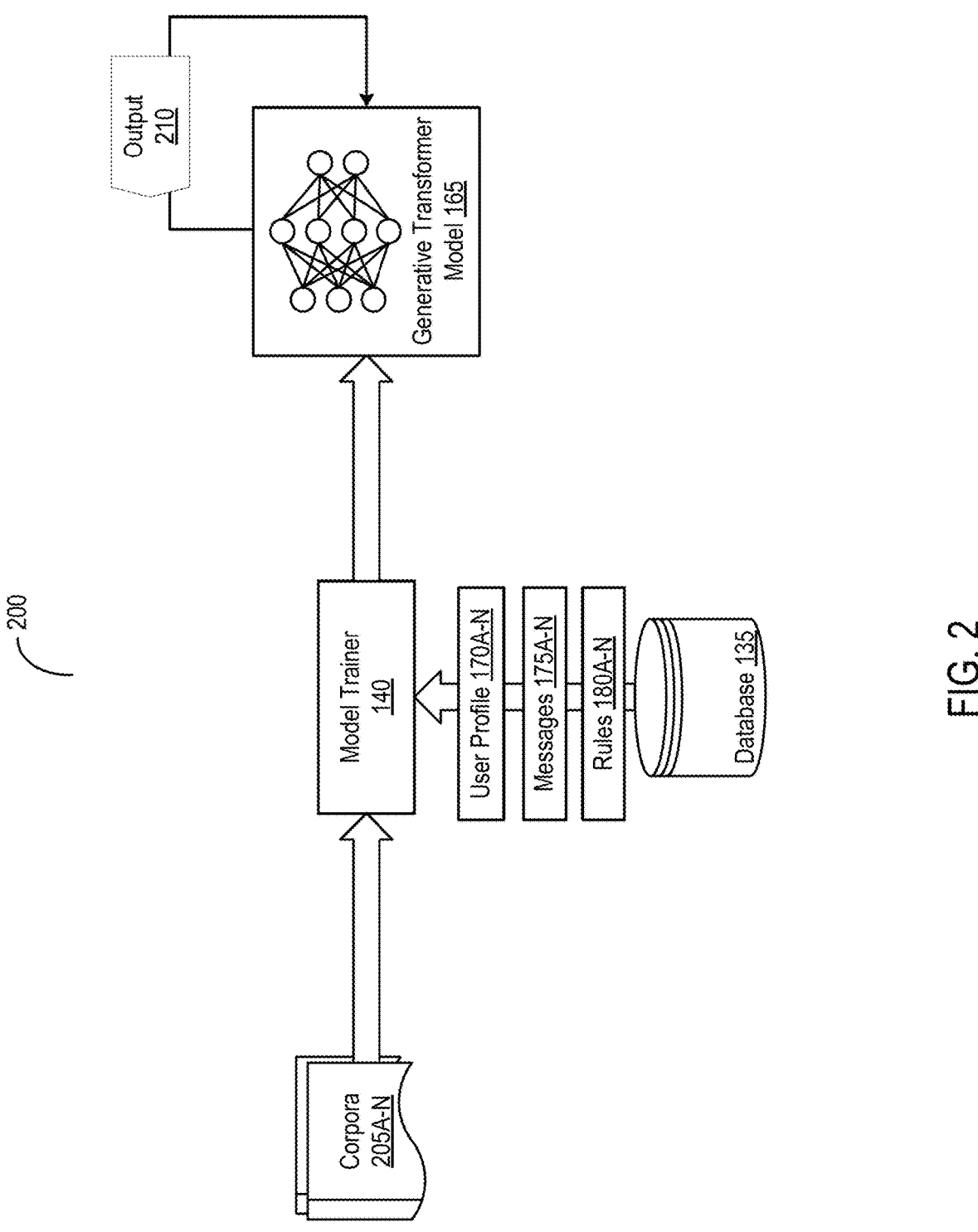
FIG. 2 depicts a block diagram for a process to train a generative transformer model in the system for generating targeted messages in accordance with an illustrative embodiment.

Referring now to FIG. 2, depicted is a block diagram for a process 200 to train a generative transformer model in the system 100 for generating targeted messages. The process 200 may include or correspond to operations performed in the system 100 to train the generative transformer model 175. Under process 200, the model trainer 140 executing on the session management system 105 can retrieve, receive, or identify a set of corpora 205A-N (hereinafter referred to as corpus 205). Each corpus 205 can identify or include a set of texts. In some embodiments, at least one of the corpora 205 can be generalized dataset. For instance, the generalized text for the corpus 205 can be obtained from a large and unstructured set of text without any focus to a particular knowledge domain. In some embodiments, at least one of the corpora 205 can include knowledge domain-specific dataset. The knowledge domain-specific dataset may include a set of strings identifying a set of conditions (e.g., related indications such as atopic dermatitis, eczema, and psoriasis for skin pathologies) to be addressed and another set of strings defining a set of endpoints (e.g., completion of activities and taking of medicines) regarding at least one of the conditions. For example, the corpus 205 can include a set of texts obtained from clinical research, medical journals, or web pages describing a particular condition (e.g., schizophrenia, multiple sclerosis, or eczema) associated with users and a set of activities to perform that will assist in alleviating or treating the condition. The knowledge domain-specific text can also be taken from at least a subset of the messages 175 on the database 135.

In some embodiments, at least one of the corpora 205 can include an association between text and content in another modality, such as an image, audio, video, or multimedia content, among others. The association between the text and the content in the other modality can be from a generalized source. For example, the generalized source for the corpus 205 can be obtained from a large, predefined corpus identifying associations among words and images. The association between the text and the content in the other modality can be from a knowledge domain-specific source. For instance, the association for the corpus 205 can be taken from clinical research, medical journals, or web pages with text and the content in the other modality.

The model trainer 140 may access the database 135 to retrieve, obtain, or otherwise identify data to be used to train the generative transformer model 175. In some embodiments, the model trainer 140 may retrieve or identify one or more user profiles 170 from the database 1135. From each user profile 170, the model trainer 140 can extract or identify information about a given user, such as a user identifier, the condition to be addressed, information on sessions conducted by the user, message preferences, user demographic information, and progress in addressing the condition, among others. In some embodiments, the model trainer 140 can retrieve or identify the set of rules 180 from the database 135. As discussed above, each rule 180 can specify a selection of messages 175 based on user behavior, user preferences, or profile information for a given user.

In some embodiments, the model trainer 140 can retrieve or identify the set of messages 175 stored in the database 135. From each message 175, the model trainer 140 can extract or identify the content (e.g., text, images, audio, or multimedia content) to be presented through the message 175. In some embodiments, the model trainer 140 may access the database 135 to retrieve or identify a set of responses (or feedback data derived therefrom) by users to previously provided messages 175. Each response may define or identify a performance of an activity by a user via the application 120 in response to presentation of a corresponding message 175. For instance, the response may include an indication of whether the user performed the specified activity, an indication of favorable reaction with the message 175, one or more interactions in response to presentation of the message 175 (e.g., user interaction via the UI elements 130 or a hyperlink included in the message 175), and a time stamp identifying performance of response, among others.

Using the data retrieved from the database 135, the model trainer 140 can produce, write, or otherwise generate at least one additional corpus 205 with which to train the generative transformer model 175. In some embodiments, the model trainer 140 can insert, include, or otherwise add the data retrieved from the database 135 into one or more of the set of corpora 205. The generated corpus 205 can include at least a portion of the user profile 170, at least a portion of the messages 175, at least a portion of the rule 180, or at least a portion of the responses, or any combination thereof, among others. In some embodiments, the model trainer 140 can generate the corpus 205 using the information extracted from the user profile 170. For instance, the corpus 205 generated using in part the information from the user profile 170 can include a set of strings describing the user's condition (e.g., an indication or disorder to be addressed via the application 120) or state (e.g., progress in completing activities or lessons), messages 175 provided to the user, and the efficacy of the messages 175 with respect to the alleviation of the condition, among others.

In some embodiments, the model trainer 140 can generate the corpus 205 using the messages 175. For example, the corpus 205 generated using the messages 175 can include an association between the condition of the user which the message 175 is to address and the content within the message 175 itself. In some embodiments, the model trainer 140 can generate the corpus 205 using the rule 180. For example, the corpus 205 generated in part using the rule 180 can include a textual description of the logic defined by the rule 180 to select the messages 175. In some embodiments, the model trainer 140 can generate the corpus 205 using the responses from users. For instance, the corpus 205 generated in part using the responses can include a set of strings identifying the content of the message 175 and the indication of whether a user performed the specified activity when presented with message 175.

With the identification, the model trainer 140 can establish or train the generative transformer model 175 using the set of corpora 205. In some embodiments, the model trainer 140 can initialize the generative transformer model 175. For example, the model trainer 140 can instantiate the generative transformer model 175 by assigning random values to the weights within the layers. In some embodiments, the model trainer 140 can fine-tune a pre-trained generative transformer model 175 (e.g., ChatGPT, DALL•E 2, and Stable Diffusion models) using the set of corpora 205. To train or fine-tune, the model trainer 140 can define, select, or otherwise identify at least a portion of each corpus 205 as a source set and at least a portion of each corpus 205 as a destination set. In some embodiments, the corpus 205 can identify or include a definition of the source set and the destination set. The source set may be used as input into the generative transformer model 165 to produce an output to be compared against the destination set. The portions of each corpus 205 can at least partially overlap and may correspond to a subset of text strings within the corpus 205. For example, when the corpus 205 contains text from messages 175 related to a particular condition, the input set may correspond to textual description of the condition and the output set may correspond to textual strings of activities to perform, lessons to engage with, reminders to take medication, or notifications to perform a particular activity, among others. The portions of the corpus 205 corresponding to the input and destination sets may lack overlap. For instance, when the corpus 205 contains an association between text and images, the portion of the corpus 205 used as the input may correspond to the text, and the portion of the corpus 205 used as the destination may correspond to the image associated with the text.

For each corpus 205, the model trainer 140 can feed or apply the strings of the source set from the corpus 205 into the generative transformer model 165. In applying, the model trainer 140 can process the input strings in accordance with the set of layers in the generative transformer model 165. As discussed above, the generative transformer model 165 may include the tokenization layer, the input embedding layer, the position encoder, the encoder stack, the decoder stack, and the output layer, among others. The model trainer 140 may process the input strings (words or phrases in the form of alphanumeric characters) of the source set using the tokenizer layer of the generative transformer model 165 to generate a set of word vectors for the input set. Each word vector may be a vector representation of at least one corresponding string in an n-dimensional feature space (e.g., using a word embedding table). The model trainer 140 may apply the set of word vectors to the input embedding layer to generate a corresponding set of embeddings. The model trainer 140 may identify a position of each string within the set of strings of the source set. With the identification, the model trainer 140 can apply the position encoder to the position of each string to generate a positional encoding for each embedding corresponding to the string and by extension the embedding.

The model trainer 140 may apply the set of embeddings along with the corresponding set of positional encodings generated from the input set of the corpus 205 to the encoder stack of the generative transformer model 165. In applying, the model trainer 140 may process the set of embeddings along with the corresponding set of positional encodings in accordance with the layers (e.g., the attention layer and the feed-forward layer) in each encoder in the encoder block. From the processing, the model trainer 140 may generate another set of embeddings to feed forward to the encoders in the encoder stack. The model trainer 140 may then feed the output of the encoder stack to the decoder stack.

In conjunction, the model trainer 140 may process the data (e.g., text, image, audio, video, or multimedia content) of the destination set using a separate tokenizer layer of the generative transformer model 165 to generate a set of word vectors for the destination set. The data of the destination set may be of the same modality as the source set of the corpus 205 or may be of a different modality as the source set of the corpus 205. Each word vector may be a vector representation of at least one corresponding string in an n-dimensional feature space (e.g., using a word embedding table). The model trainer 140 may apply the set of word vectors to the input embedding layer to generate a corresponding set of embeddings. The model trainer 140 may identify a position of each string within the set of strings of the target set. With the identification, the model trainer 140 can apply the position encoder to the position of each string to generate a positional encoding for each embedding corresponding to the string and by extension the embedding.

The model trainer 140 may apply the set of embeddings along with the corresponding set of positional encodings generated from the destination set of the corpus 205 to the decoder stack of the generative transformer model 165. The model trainer 140 may also combine the output of the encoder stack in processing through the decoder stack. In applying, the model trainer 140 may process the set of embeddings along with the corresponding set of positional encodings in accordance with the layers (e.g., the attention layer, the encoder-decoder attention layer, the feed-forward layer) in each decoder in the decoder block. The model trainer 140 may combine the output from the encoder with the input of the encoder-decoder attention layer in the decoder block. From the processing, the model trainer 140 may generate an output set of embeddings to be fed forward to the output layer.

Continuing on, the model trainer 140 may feed the output from the decoder block into the output layer of the generative transformer layer 165. In feeding, the model trainer 140 may process the embeddings from the decoder block in accordance with the linear layer and the activation layer of the output layer. With the processing, the model trainer 140 may calculate probability for each embedding. The probability may represent a likelihood of occurrence for an output, given an input token. Based on the probabilities, the model trainer 140 may select an output token (e.g., at least a portion of output text, image, audio, video, or multimedia content with the highest probability) to form, produce, or otherwise generate output 210. The output 210 can include text content, image content, audio content, video content, or multimedia content, among others, or any combination thereof. The output 210 can be in the same modality as the target set of the corpus 205. While described primarily in terms of transformer model architecture, other architectures can be used for the generative transformer model 165 to output content.

With the generation, the model trainer 140 can compare the output 210 from the generative transformer model 165 with the destination set of the corpus 205 used to generate the output 210. The comparison can be between the probabilities (or distribution) of various tokens for the content (e.g., words for text output) from the output 210 versus the probabilities of tokens in the target set of the corpus 205. For instance, the model trainer 140 can determine a difference between a probability distribution of the output 210 versus the target set of the corpus 205 to compare. The probability distribution may identify a probability for each candidate token in the output 210 or the token in the target set of the corpus 205. Based on the comparison, the model trainer 140 can calculate, determine, or otherwise generate a loss metric. The loss metric may indicate a degree of deviation of the output 210 from the expected output as defined by the target set of the corpus 205 used to generate the output 210. The loss metric may be calculated in accordance with any number of loss functions, such as a norm loss (e.g., L1 or L2), mean squared error (MSE), quadratic loss, cross-entropy loss, or Huber loss, among others.

In some embodiments, the model trainer 140 may determine the loss metric for the output 210 based on the data retrieved from the database 135. In determining, the model trainer 140 may compare the content of the output 210 with messages 175 to calculate a degree of similarity. The degree of similarity may measure, correspond to, or indicate, for example, a level of semantic similarity (e.g., using a knowledge map when comparing between text of the message 175 and output 210), visual similarity (e.g., pixel to pixel value comparison, when comparing between image or frames of the video of the message 175 and output 210), or audio similarity (e.g., using a correlation or cosine similarity measure between the audio of the message 175 and the output 210). The loss metric may be a function of the degree of similarity, rule 180, or responses indicating whether users responded to the message 175 with which the output 210 is compared to, among others. In general, the higher the loss metric, the more the generated output message may have deviated from the preference established by a given user or in contrivance of one of the rules 180. Conversely, the lower the loss metric, the less the generated output message may have deviated from the preference established by a given user and be in conformance with one or more of the rules 180. The loss metric may be calculated to train the generative transformer model 165 to generate output content for messages with a higher probability of engagement by the user.

Using the loss metric, the model trainer 140 can update one or more weights in the set of layers of the generative transformer model 165. The updating of the weights may be in accordance with a back propagation and optimization function (sometimes referred to herein as an objective function) with one or more parameters (e.g., learning rate, momentum, weight decay, and number of iterations). The optimization function may define one or more parameters at which the weights of the generative transformer model 165 are to be updated. The optimization function may be in accordance with stochastic gradient descent, and may include, for example, an adaptive moment estimation (Adam), implicit update (ISGD), and adaptive gradient algorithm (AdaGrad), among others. The model trainer 140 can iteratively train the generative transformer model 165 until convergence. Upon convergence, the model trainer 140 can store and maintain the set of weights for the set of layers of the generative transformer model 165 for use in inference stage.

Figure 3:
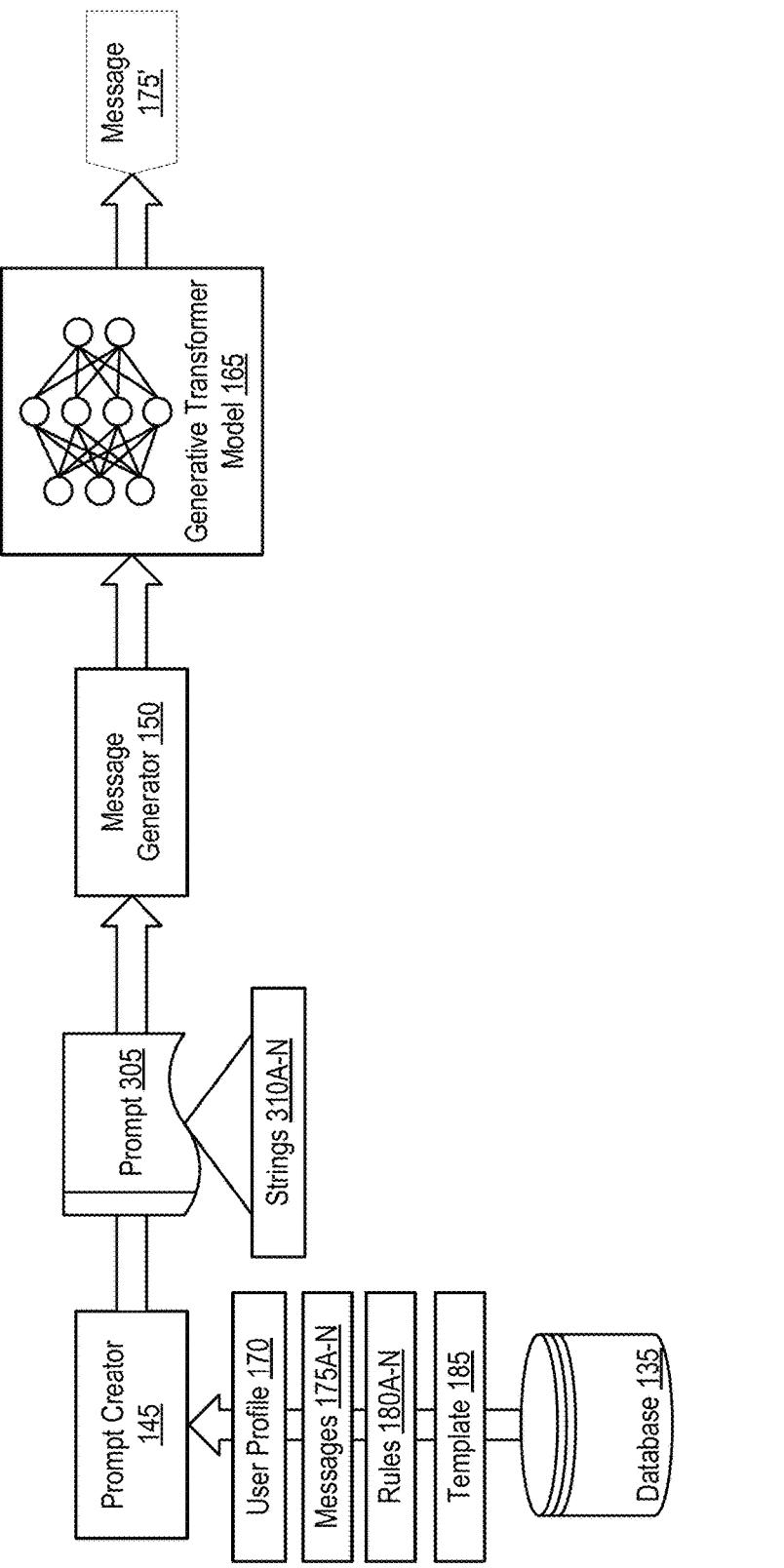
FIG. 3 depicts a block diagram for a process to apply prompts to a generative transformer model to generate messages in the system for generating targeted messages in accordance with an illustrative embodiment.

Referring now to FIG. 3, depicted is a block diagram for a process 300 to apply prompts to a generative transformer model to generate messages in the system 100 for generating targeted messages. The process 300 may include or correspond to operations performed in the system 100 to generate messages using the generative transformer model 165. Under process 300, the prompt creator 145 executing on the session management system 105 can retrieve, obtain, or otherwise identify the user profile 170 from the database 135. The user profile 170 may be for a given user associated with the user device 110 to which a newly generated message is to be provided for presentation. From the user profile 170, the prompt creator 145 may extract or identify the condition to be addressed. The prompt creator 145 may also identify the user identifier (e.g., name), information on sessions conducted by the user, activity log, message preferences, user trait information, and progress in addressing the condition, among others. In some embodiments, the prompt creator 145 may identify the activity log for the user associated with the user profile 170.

In some embodiments, the prompt creator 145 can access the database 135 to retrieve or identify one or more messages 175. The prompt creator 145 can select the one or more messages 175 based on information identified from the user profile 170, such as the endpoint towards which to achieve for the user to address the condition. For instance, the prompt creator 145 may identify a subset of messages 175 related to the condition of smoking and an endpoint of performing a walking exercise, as identified from the user profile 170. In some embodiments, the prompt creator 145 may retrieve or identify at least one rule 180 from the database 135. The prompt creator 145 can select the at least one rule 180 based on information identified from the user profile 170. For instance, the prompt creator 145 may identify a rule for selecting messages 175 specifying that the user has the condition of affective disorder, is three weeks into the therapy regimen, and is at a medium difficulty level.

In conjunction, the prompt creator 145 can retrieve, select, or otherwise identify at least one template 185 from the database 135. The identification of the template 185 from the set of templates 185 based on the information from the user profile 170, such as the condition to be addressed, activity log, user trait, user identifier, message preferences, information on sessions conducted by the user, and progress in addressing the condition, among others. In some embodiments, the prompt creator 145 may select the template 185 based on the training of the generative transformer model 165. When the generative transformer model 165 has been trained on general corpora 205, the prompt creator 145 may select the template 185 including placeholders for messages 175. When the generative transformer model 165 has been trained on the knowledge domain-specific corpora 205, the prompt creator 145 may identify the template 185 lacking placeholders for messages 175.

With the identification, the prompt creator 145 may write, produce, or otherwise generate at least one prompt 305 using the information from the user profile 170 and the one or more parameters in accordance with the template 185. The parameters may be used to define the generation of messages to be presented to the user. The prompt creator 145 may determine or identify the parameters using the messages 175 or the rules 180, among others. In some embodiments, the prompt creator 145 may include at least a portion of the content of the messages 175 (e.g., text, image, audio, video, or multimedia content) as a portion of the parameters. For instance, the prompt creator 145 may use content from the set of messages 175 as a portion of the parameters used to generate new messages. The parameters may identify the set of messages 175 as candidate messages from which to select for generating the new message. In some embodiments, the prompt creator 145 may identify the logic for selection as defined in the rule 180 for selecting messages 175 as a portion of the parameters. For example, the prompt creator 145 may identify a time at which to present the message 175 from the rule 180.

In generating, the prompt creator 145 may add, insert, or otherwise include the information from the user profile 175 and the one or more parameters into the placeholders with the template 185. As discussed above, the template 185 may include a set of defined strings and one or more placeholders to be inserted among the strings for input to the generative transformer model 165. The string may correspond to predefined, fixed text to be included as part of the input prompt for the generative transformer model 165. The template 185 may define at least one placeholder as where information from the user profile 175 is to be inserted and at least one other placeholder as where the one or more parameters for defining the messages is to be inserted. The prompt creator 145 may parse the template 185 to find or identify the placeholders therein. For each placeholder, if the placeholder defines at least a portion of the information from the user profile 170 is to be inserted, the prompt creator 145 may include the portion of information from the user profile 170 into the placeholder. If the placeholder defines at least a portion of the one or more parameters is to be inserted, the prompt creator 145 may include the portion of one or more parameters into the placeholder of the template 185. By traversing through the template 185 and inserting data into the placeholders, the prompt creator 145 may form and construct the prompt 305.

The prompt 305 can include a set of strings 310A-N (hereinafter generally referred to as strings 310A-N) to be fed into the message generator 150 to generate the message for a given user. The set of strings 310 may be a combination of the predefined set of strings originally included in the template 185, as well as the information from the user profile 170 and the one or more parameters defining generation of new messages. For example, the user profile 170 may define a user who has chronic migraine headaches to be addressed, and the activity log for the user may identify that the user has drunk 96 mL of water, eaten 2 meals for the day, and had 5 migraine headaches in the last 2 months. The prompt 305 generated with this user profile 170 may have the set of strings 310 including "Given a Chronic Migraine sufferer who drank 96 mL of water today, ate 2 meals today. She is making good progress through lessons A, B, C, D and reduced her headaches to 5 times in the last 2 months. Can you help me generate a message to help her finish a lesson (Lesson E) and continue to monitor her intake?" Upon completion, the prompt creator 145 may convey, pass, or otherwise provide the prompt 305 to the message generator 150.

With the generation, the message generator 150 may feed or apply the prompt 305 to the generative transformer model 165. In applying, the message generator 150 can process the set of strings 310 of the prompt 305 using the set of layers in the generative transformer model 165. As discussed above, the generative transformer model 165 may include the tokenization layer, the input embedding layer, the position encoder, the encoder stack, the decoder stack, and the output layer, among others. The message generator 150 may process the input strings 310 (words or phrases in the form of alphanumeric characters) of the prompt 305 using the tokenizer layer of the generative transformer model 165 to generate a set of word vectors (sometimes herein referred to as word tokens or tokens) for the input set. Each word vector may be a vector representation of at least one corresponding string 310 in an n-dimensional feature space (e.g., using a word embedding table). The message generator 150 may apply the set of word vectors to the input embedding layer to generate a corresponding set of embeddings. The message generator 150 may identify a position of each string within the set of strings 310 of the prompt 305. With the identification, the message generator 150 can apply the position encoder to the position of each string to generate a positional encoding for each embedding corresponding to the string and by extension the embedding.

The message generator 150 may apply the set of embeddings along with the corresponding set of positional encodings generated from the input set of the corpus 205 to the encoder stack of the generative transformer model 165. In applying, the message generator 150 may process the set of embeddings along with the corresponding set of positional encodings in accordance with the layers (e.g., the attention layer and the feed-forward layer) in each encoder in the encoder block. From the processing, the message generator 150 may generate another set of embeddings to feed forward to the encoders in the encoder stack. The message generator 150 may then feed the output of the encoder stack to the decoder stack.

In conjunction, the message generator 150 may input an initiation input (sometimes referred to herein as a start token) using a separate tokenizer layer of the generative transformer model 165 to generate one or more word vectors. Each word vector may be a vector representation of at least one corresponding string in an n-dimensional feature space (e.g., using a word embedding table). The message generator 150 may apply the set of word vectors to the input embedding layer to generate a corresponding set of embeddings. The message generator 150 may identify a position of each string within the set of strings of the target set. With the identification, the message generator 150 can apply the position encoder to the position of each string to generate a positional encoding for each embedding corresponding to the string and by extension the embedding.

The message generator 150 may apply the set of embeddings along with the corresponding set of positional encodings generated from the decoder stack of the generative transformer model 165. The message generator 150 may also combine the output of the encoder stack in processing through the decoder stack. In applying, the message generator 150 may process the set of embeddings along with the corresponding set of positional encodings in accordance with the layers (e.g., the attention layer, the encoder-decoder attention layer, the feed-forward layer) in each decoder in the decoder block. The message generator 150 may combine the output from the encoder with the input of the encoder-decoder attention layer in the decoder block. From the processing, the message generator 150 may generate an output set of embeddings to be fed forward to the output layer.

Continuing on, the message generator 150 may feed the output from the decoder block into the output layer of the generative transformer layer 165. In feeding, the message generator 150 may process the embeddings from the decoder block in accordance with the linear layer and the activation layer of the output layer. With the processing, the message generator 150 may calculate a probability for each embedding. The probability may represent a likelihood of occurrence for an output, given an input token. Based on the probabilities, the message generator 150 may select an output token (e.g., at least a portion of output text, image, audio, video, or multimedia content with the highest probability) to form, produce, or otherwise generate at least a portion of the message 175'. The message generator 150 may repeat the above-described processing using the layers of the generative transformer model 165 to form the entirety of message 175'. The message 175' output by the generative transformer model 165 can include text content, image content, audio content, video content, or multimedia content, among others, or any combination thereof.

From applying, the message generator 150 can produce or generate the new message 175' from the generative transformer model 165. The message 175' may identify at least one activity towards achieving an endpoint to address the condition of the user. For example, the prompt 305 may state, "Given a Chronic Migraine sufferer who drank 96 mL of water today, ate 2 meals today. He is making satisfactory progress through lessons A, B, C, D and reduced his headaches to 5 times in the last 2 months. Can you help me generate a message to help him finish a lesson (Lesson E) and continue to monitor his intake?" The generated message 175' may state, "Hi! How are you? You have consumed 96 mL of water today and eaten 2 meals today! You're doing great! Since following lessons A, B, C, and D, only 5 migraines have occurred in the last 2 months. Continue to reach your water and caloric intake goals and let's make it past these migraines! Don't forget to continue working through Lesson E. Keep up the good work!" In some embodiments, the message 175' may be for a lesson and may identify information for presentation to the user. For example, the message 175' can include an explanation on the influence of water and calorie intake with respect to migraines. The message 175' may include new content and may differ from the content included in stored messages 175 on the database 135 that may have been manually created.

In some embodiments, in applying the prompt 305, the message generator 150 can identify or select at least one of the messages 175' from the set of messages 175 included in the strings 310 of the prompt 305. The prompt 305 used to select one of the set of messages 175 may include the content of each message 175 as one of the parameters. For example, the prompt 305 may state "Given Tom has not smoked for 3 days, can you help me choose the best message from below to encourage Tom to not smoke? (A) Congratulations for the achievement so far. Keep going strong. (B) 3 days in a row is great, continue to stay disciplined when you feel the need to smoke. (C) How are you feeling today? Distractions are a great way to not feel the urge to smoke." By applying the prompt 305, the message generator 150 may process the strings 310 of the prompt 305 to select one of the candidate set of messages 175 as the message 175'.

In some embodiments, the message 175' generated by the generative transformer model 165 can contain text content, image content, audio content, video content, or multimedia content, among others, or any combination thereof. For example, the presentation of the message 175' may include an image of a smiley face to further encourage a user to complete their goals. Furthermore, the message 175' may include a video clip of a loved one, a motivational speaker, a medical professional, an influencer, or a therapist, among others, or any combination thereof. The multimedia content (e.g., video podcasts, audio slideshows, or animated videos, among others) of the message 175' may further educate a user on the user's condition, encourage a user, or entertain the user of the application 120.

With the generation, the message generator 150 can store and maintain an association between the message 175' and the user on the database 135. The association may use one or more data structures stored on the database 135, using one or more data structures (e.g., an array, a matrix, a list, a table, a heap, or a tree). The association may be between the user profile 170 associated with the user to which the message 175' is to be provided and the message 175'. The message generator 150 may generate multiple messages 175', prior to provision and presentation to the user associated with the user profile 170.

Figure 4:
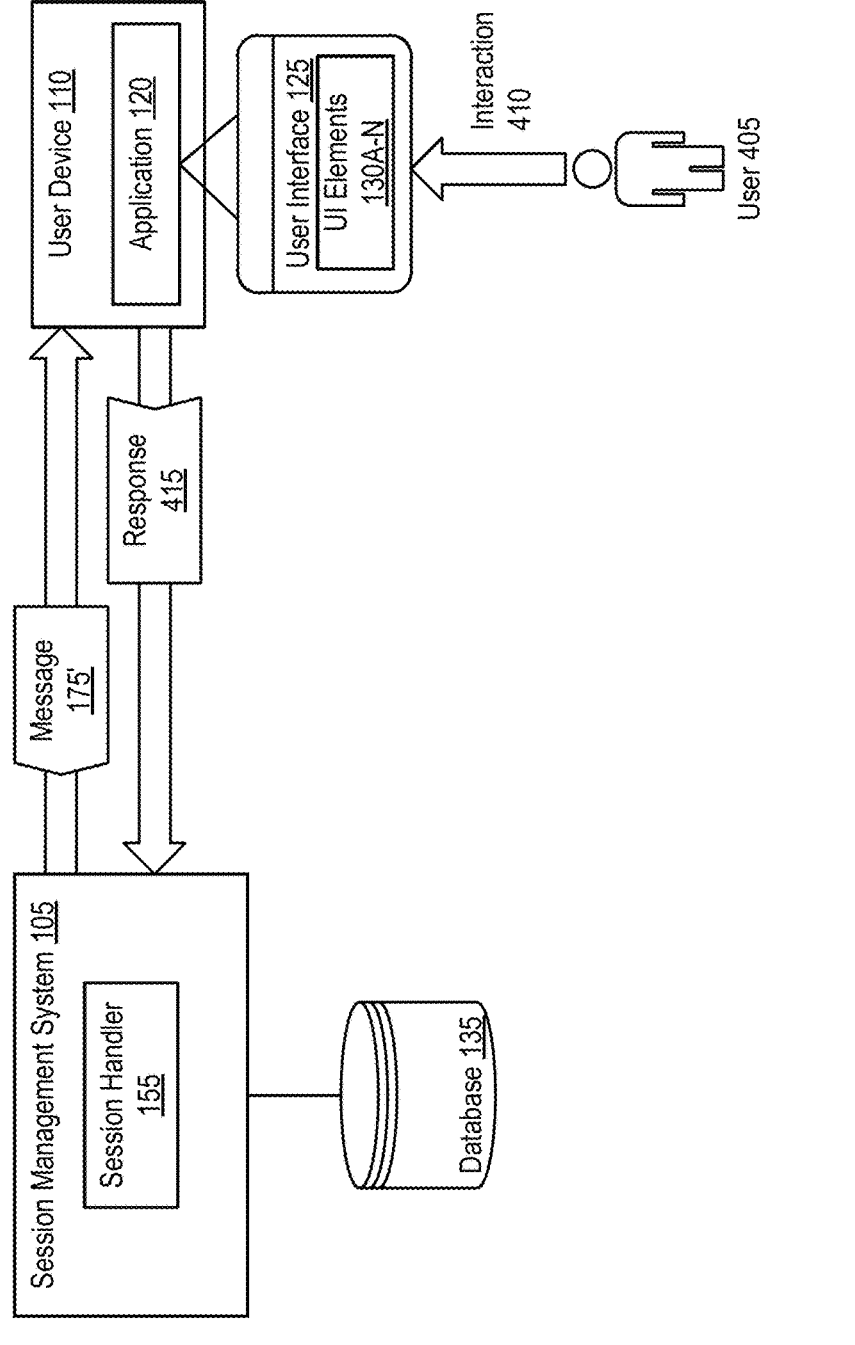
FIG. 4 depicts a block diagram for a process to transmit a message to a user device in the system for generating targeted messages in accordance with an illustrative embodiment.

Referring now to FIG. 4, depicted is a block diagram for a process 400 to transmit a message to the user device 110 in the system 100 for generating targeted messages. The process 400 may include or correspond to operations performed in the system 100 to run a session in which messages are provided to a user device and responses are collected from the user device. Under the process 400, the session handler 155 executing on the session management system 105 may send, transmit, or otherwise provide the message 175' to the user device 110 associated with a user 410. For the user 410, the session handler 155 may access the database 135 to retrieve or identify the user profile 170 for the user 405 of the application 120 on the user device 110. From the user profile 170, the session manager 155 may determine or identify the respective message 175' for the user 405 and transmit the message 175' to the user device 110 for the application 120.

In some embodiments, the session handler 155 may receive a request from the user device 110 to be provided with a new message. The request may have been generated by the application 120 in response to interactions by the user 405 to call for a new message. The request may identify information about the user 405, such as user identifier (e.g., username or account identifier), authentication credentials, device identifier, network address, among others. The session handler 155 may use the information received from the application 120 to find the respective user profile 170 of the user 405. With the identification of the user profile 170, the session handler 155 may identify one or more messages 175' associated with the user profile 150.

In some embodiments, the session handler 155 can calculate, identify, or otherwise determine a time at which to send the message 175' to the user device 110. In some embodiments, the session handler 155 can use a delivery model for the user 405. The delivery model may define a set of times at which to send one or more messages 175' for presentation via the user device 110. When the current time corresponds to one of the times defined by the delivery model, the session handler 155 may determine to provide the message 175' at the current time. In some embodiments, the session handler 155 may use the user profile 170 to determine the time at which to transmit the message 175'. The user profile 170 may identify the message preferences for the user 405, such as a time at which to send the message 175' to the user device 110. When the current time satisfies the message preferences (e.g., within the time preference), the session handler 155 may determine to transmit the message 175' to the user device 110.

To transmit, the session handler 155 may generate at least one instruction for presenting the message 175' to transmit to the user device 110. The instruction can include the contents of the message 175' or an identifier for the message 175'. In some embodiments, the instruction may be code, data packets, or a control to present a message to the user 405. The instruction may include processing instructions for display of the message 175' on the application 120 through the UI elements 130 of the user interface 125 (e.g., as an in-application message). The instruction may also include instructions for the user 405 to perform in relation to their session. For example, the instruction may display the message 175' instructing the user 405 to perform a certain activity associated with their session. In some embodiments, the instructions may be in accordance with a messaging protocol, such as a short message service (SMS) or a multimedia messaging service (MMS). The instruction may identify the user device 110 (e.g., using a phone number or network address) to which to transmit the message 175', as well as the content of the message 175' in a payload. Upon generation, the session handler 155 can send the instruction to the user device 110 via the network 115.

Upon receipt, the user device 110 can render, display, or otherwise present the message 175' via a display. For example, when the message 175' is delivered in accordance with a messaging protocol (e.g., SMS and MMS), the user device 110 may invoke a messaging application (e.g., the application 120 or another application) to present the message 175'. The messaging application may include a user interface (e.g., similar to the user interface 125) to display the contents of the message 175'. In some embodiments, the application 120 (e.g., the digital therapeutic application) on the user device 110 may render, display, or otherwise present the message 175' via the user interface 125. For example, the instructions for the message 175' may specify, identify, or define a layout (e.g., positioning, size, and color) for individual UI elements 130 when the message 175' is presented via the user interface 125 of the application 120.

With the presentation, the user device 110 may monitor for at least one interaction 410 by the user 405 in response to the presentation of the message 175'. In some embodiments, the user device 110 may use the messaging application to monitor for interactions 410 with the message 175' when presented via the display of the user device 110. For example, the messaging application may have event listeners to monitor for a click event on a link that is part of the message 175' upon presentation. In some embodiments, the application 120 on the user device 110 may monitor for one or more interactions 410 by the user 405 with the UI elements 130 of the user interface 125, in response to presentation of the message 175'. The interaction 410 may be concurrent with the presentation of the message 175'. For example, the interaction 410 may correspond to an interaction to play a video clip included in the message 175' through a play button on the application 120. In some embodiments, the interaction 410 may be subsequent to the presentation of the message 175' on the user device 110. For instance, the interaction 410 may correspond to a set of user interactions to log a completion of a specified activity, after presentation of the message 175' prompting the user 405 to perform the specified activity. The interaction 410 may also include data (e.g., text) inputted by the user 405 in response to the prompt of the message 175'.

Upon detection of the interaction 410, the user device 110 may output, produce, or generate at least one response 415 for transmission to the session management system 105. The response 415 may indicate, include, or otherwise identify performance of the activity by the user 405 via the user device 110 in response to presentation of the message 175'. In some embodiments, the application 120 on the user device 110 may generate the response 415 using the detected interaction 410. The response 415 may identify an event associated with the interaction 410 for the performance of the activity by the user 405, a time stamp for the presentation of the message 175', a time stamp for the event, and an identifier for the user 405, among other information. The response 415 may also include data inputted by the user 405 via the user interface 125 of the application 120. In some embodiments, the application 120 may maintain a timer to keep track of time elapsed since presentation of the message 175'. The application 120 may compare the elapsed time with a time limit for the message 175'. When the elapsed time exceeds the time limit, the application 120 may generate the response 415 to indicate no user interaction with the message 175'. With the generation, the application 120 may provide, transmit, or otherwise send the response 415 to the session management system 105.

Figure 5:
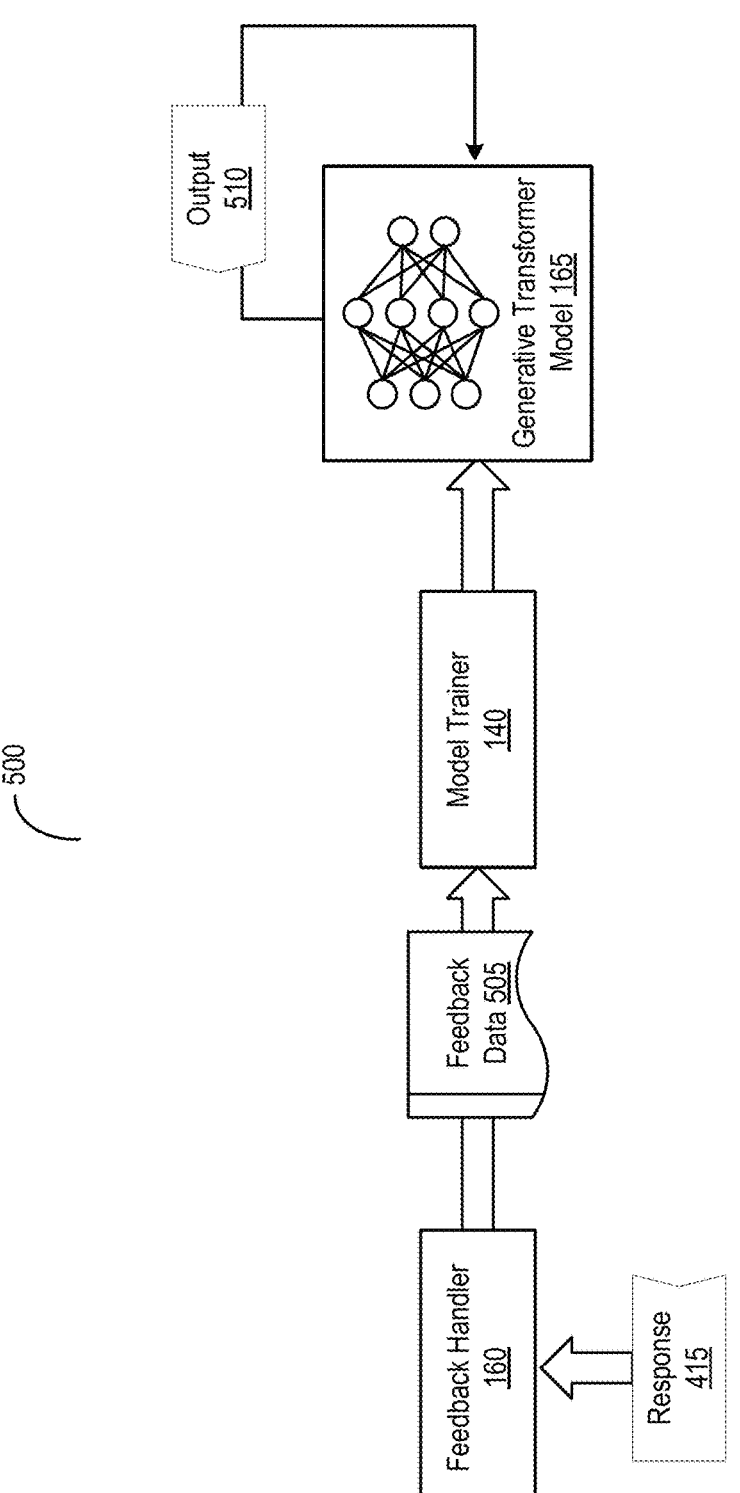
FIG. 5 depicts a block diagram for a process to update generative transformer models in the system for generating targeted messages in accordance with an illustrative embodiment.

Referring now to FIG. 5, depicted is a block diagram for a process 500 to update generative transformer models in the system 100 for generating targeted messages. The process 500 may include or correspond to operations to derive feedback data gathered from the response 415 to update the generative transformer model 165. Under process 500, the feedback handler 160 executing on the session management system 105 may retrieve, identify, or otherwise receive the response 415 from the user device 110. Upon receipt, the feedback handler 160 may parse the response 415 to extract or identify the information included therein. From the response 415, the feedback handler 160 may determine or identify the performance of the activity by the user 405 via the user device 110 (or the application 120) in response to presentation of the message 175'. The feedback handler 160 may identify whether the user 405 performed the specified activity or interaction 410 associated with the activity. In some embodiments, the feedback handler 160 may identify the event associated with the performance of the activity, the time stamp for the event, the data inputted by the user 405, and other information included in the response 415.

Based on the response 415, the feedback handler 160 may produce, create, or otherwise generate feedback data 505. In some embodiments, the feedback handler 160 may generate the feedback data 505 for subsequent generation of messages 175' by the generative transformer model 165. In some embodiments, the feedback data 505 may identify or include information to be used as one or more parameters defining subsequent messages to be generated and presented for the user 405. For example, for a subsequent message 175', the prompt creator 145 may insert the feedback data 505 into designated placeholders in the template 185 to generate a new prompt 305 to feed to the generative transformer model 165. The feedback data 505 may indicate or include whether the user 405 had responded to the presentation of the message 175' and the time of the response. Upon generation, the feedback handler 160 may store and maintain an association between the feedback data 505 and the user profile 170 on the database 135.

In some embodiments, the feedback handler 165 may generate the feedback data 505 to include information to be used to update the weights of the generative transformer model 165. In some embodiments, the feedback handler 165 may generate the feedback data 505 in a similar format as the corpus 205 described above. The feedback data 505 may be generated to include the contents of the message 175' and the information from the response 415 from the user 405. In some embodiments, the feedback handler 165 may calculate, generate, or otherwise determine a performance metric identifying or corresponding to the interaction 410 of the user 405 with the message 175' to include as part of the feedback data 505. The performance measure may indicate a degree to which the presented message 175' elicits the interaction. In general, more interactions with the variant of the message 175' may result in a higher performance measure. In contrast, less or no interactions with the message 175' when presented may result in a lower performance measure. Upon generation, the feedback handler 165 may include the performance metrics and the contents of the message 175' into the feedback data 505.

In some embodiments, the feedback handler 160 may apply sentiment analysis to the information included in the response 415 (e.g., the data inputted by the user 405) to generate the performance metric. The sentiment analysis may be performed using natural language processing (NLP) techniques, such as lexicon analysis for sentiment related words, a support vector machine (SVM), linear regression, or Naïve Bayesian model, among others. The feedback handler 160 may apply the sentiment analysis algorithm to the response 415 to recognize, detect, or otherwise identify a sentiment of the user 405 with respect to the presented message 175'. The sentiment may include, for example, positive, negative, or neutral indications, among other. Using the identified sentiment, the feedback handler 160 may assign a value to the performance metric. For example, when the sentiment is positive, the feedback handler 160 may assign a high value. When the sentiment is negative, the feedback handler 160 may assign a low value. When the sentiment is neutral, the feedback handler 160 may assign an intermediate value.

The model trainer 140 may use the feedback data 505 to modify, adjust, or otherwise update the weights of the generative transformer model 165. The feedback data 505 may be aggregated over multiple responses 415 from the user 405 or from multiple users 405. In general, the model trainer 140 may update the weights to credit production of messages 175' with high performance metrics and punish outputting of messages 175' with lower performance metrics. The training or fine-tuning of the generative transformer model 165 using the feedback data 505 may be similar to the training or fine-tuning using the set of corpora 205 described above. To train, the model trainer 140 may define, select, or otherwise identify at least a portion of each feedback data 505 as a source set and at least a portion of each feedback data 505 as a destination set. The source set may be used as input into the generative transformer model 165 to produce an output to be compared against the destination set. The portions of each feedback data 505 can at least partially overlap and may correspond to a subset of text strings within the feedback data 505.

The model trainer 140 can feed or apply the strings of the source set from the feedback data 505 into the generative transformer model 165. In applying, the model trainer 140 can process the input strings in accordance with the set of layers in the generative transformer model 165. As discussed above, the generative transformer model 165 may include the tokenization layer, the input embedding layer, the position encoder, the encoder stack, the decoder stack, and the output layer, among others. The model trainer 140 may process the input strings (words or phrases in the form of alphanumeric characters) of the source set using the tokenizer layer of the generative transformer model 165 to generate a set of word vectors for the input set. Each word vector may be a vector representation of at least one corresponding string in an n-dimensional feature space (e.g., using a word embedding table). The model trainer 140 may apply the set of word vectors to the input embedding layer to generate a corresponding set of embeddings. The model trainer 140 may identify a position of each string within the set of strings of the source set. With the identification, the model trainer 140 can apply the position encoder to the position of each string to generate a positional encoding for each embedding corresponding to the string and by extension the embedding.

The model trainer 140 may apply the set of embeddings along with the corresponding set of positional encodings generated from the input set of the feedback data 505 to the encoder stack of the generative transformer model 165. In applying, the model trainer 140 may process the set of embeddings along with the corresponding set of positional encodings in accordance with the layers (e.g., the attention layer and the feed-forward layer) in each encoder in the encoder block. From the processing, the model trainer 140 may generate another set of embeddings to feed forward to the encoders in the encoder stack. The model trainer 140 may then feed the output of the encoder stack to the decoder stack.

In conjunction, the model trainer 140 may process the data (e.g., text, image, audio, video, or multimedia content) of the destination set using a separate tokenizer layer of the generative transformer model 165 to generate a set of word vectors for the destination set. The data of the destination set may be of the same modality as the source set of the feedback data 505 or may be of a different modality as the source set of the feedback data 505. Each word vector may be a vector representation of at least one corresponding string in an n-dimensional feature space (e.g., using a word embedding table). The model trainer 140 may apply the set of word vectors to the input embedding layer to generate a corresponding set of embeddings. The model trainer 140 may identify a position of each string within the set of strings of the target set. With the identification, the model trainer 140 can apply the position encoder to the position of each string to generate a positional encoding for each embedding corresponding to the string and by extension the embedding.

The model trainer 140 may apply the set of embeddings along with the corresponding set of positional encodings generated from the destination set of the feedback data 505 to the decoder stack of the generative transformer model 165. The model trainer 140 may also combine the output of the encoder stack in processing through the decoder stack. In applying, the model trainer 140 may process the set of embeddings along with the corresponding set of positional encodings in accordance with the layers (e.g., the attention layer, the encoder-decoder attention layer, the feed-forward layer) in each decoder in the decoder block. The model trainer 140 may combine the output from the encoder with the input of the encoder-decoder attention layer in the decoder block. From the processing, the model trainer 140 may generate an output set of embeddings to be fed forward to the output layer.

Continuing on, the model trainer 140 may feed the output from the decoder block into the output layer of the generative transformer layer 165. In feeding, the model trainer 140 may process the embeddings from the decoder block in accordance with the linear layer and the activation layer of the output layer. With the processing, the model trainer 140 may calculate a probability for each embedding. The probability may represent a likelihood of occurrence for an output, given an input token. Based on the probabilities, the model trainer 140 may select an output token (e.g., at least a portion of output text, image, audio, video, or multimedia content with the highest probability) to form, produce, or otherwise generate the output 510. The output 510 can include text content, image content, audio content, video content, or multimedia content, among others, or any combination thereof. The output 510 can be in the same modality as the target set of the feedback data 505.

With the generation, the model trainer 140 can compare the output 510 from the generative transformer model 165 with the destination set of the feedback data 505 used to generate the output 510. The comparison can be between the probabilities (or distribution) of various tokens for the content (e.g., words for text output) from the output 510 versus the probabilities of tokens in the target set of the feedback data 505. For instance, the model trainer 140 can determine a difference between a probability distribution of the output 510 versus the target set of the feedback data 505. The probability distribution may identify a probability for each candidate token in the output 510 or the token in the target set. Based on the comparison, the model trainer 140 can calculate, determine, or otherwise generate a loss metric. The loss metric may indicate a degree of deviation of the output 510 from the expected output as defined by the target set of the feedback data 505 used to generate the output 510. The loss metric may be calculated by in accordance with any number of loss functions, such as a norm loss (e.g., L1 or L2), a mean squared error (MSE), a quadratic loss, a cross-entropy loss, and a Huber loss, among others.

In some embodiments, the model trainer 140 may determine the loss metric for the output 510 based on the performance measures determined for each message 175'. In determining, the model trainer 140 may compare the content of the output 510 with messages 175 to calculate a degree of similarity. The degree of similarity may measure, correspond to, or indicate, for example, a level of semantic similarity (e.g., using a knowledge map when comparing between text of the message 175' and output 510), visual similarity (e.g., pixel to pixel value comparison, when comparing between image or frames of the video of the message 175' and output 510), or audio similarity (e.g., using a correlation or cosine similarity measure between the audio of the message 175' and the output 510). The loss metric may be a function of the degree of similarity and the performance measure, among others. In general, the higher the loss metric, the more the generated output 510 may have deviated away from messages 175' with higher performance metrics and closer to messages 175' with lower performance metrics. Conversely, the lower the loss metric, the less the generated output 510 may be similar to messages 175' with higher performance metrics and deviated from messages 175' with lower performance metric. The loss metric may be calculated to train the generative transformer model 165 to generate output content for messages with a higher probability of engagement by the user.

Using the loss metric, the model trainer 140 can update one or more weights in the set of layers of the generative transformer model 165. The updating of the weights may be in accordance with back propagation and optimization function (sometimes referred to herein as an objective function) with one or more parameters (e.g., learning rate, momentum, weight decay, and number of iterations). The optimization function may define one or more parameters at which the weights of the generative transformer model 165 are to be updated. The model trainer 140 can iteratively train generative transformer model 165 until convergence. Upon convergence, the model trainer 140 can store and maintain the set of weights for the set of layers of the generative transformer model 165 for use.

In this manner, the session management service 105 may iteratively and continuously factor in responses 405 from presentations of messages 175' to the user 405 to improve generation of new content for subsequent message 175'. Compared to the predefined, fixed sequence of content, the incorporation of the feedback data 505 may enable new generation of messages 175' that are more targeted and pertinent to the changing state (e.g., progression in addressing the condition) and preferences of the user 405. In the context of digital therapeutics, the new generation of the message 175' may factor in changes to the use, such as improvement or degradation of the end user's condition or progression through the therapy regimen. With the use of the generative transformer model 165, the content can be generated specifically targeting the user 405 in a flexible manner and can scale the individualization of content to a large audience. The enablement of flexibility, scalability, and specificity can optimize or reduce consumption of computing resources (e.g., processor and memory) and network bandwidth that would have been otherwise wasted by providing ineffective content. From a human-computer interaction (HCI) perspective, the content generated by leveraging the generative transformer model 165 can yield higher quality of interactions by the user 405 with the user device 110. In addition, the increase in engagement can result in higher levels of adherence of the user 405 with the therapy regimen. The higher adherence in turn may lead to a greater likelihood of preventing, alleviating, or treating conditions of the end-user.

Figure 6:
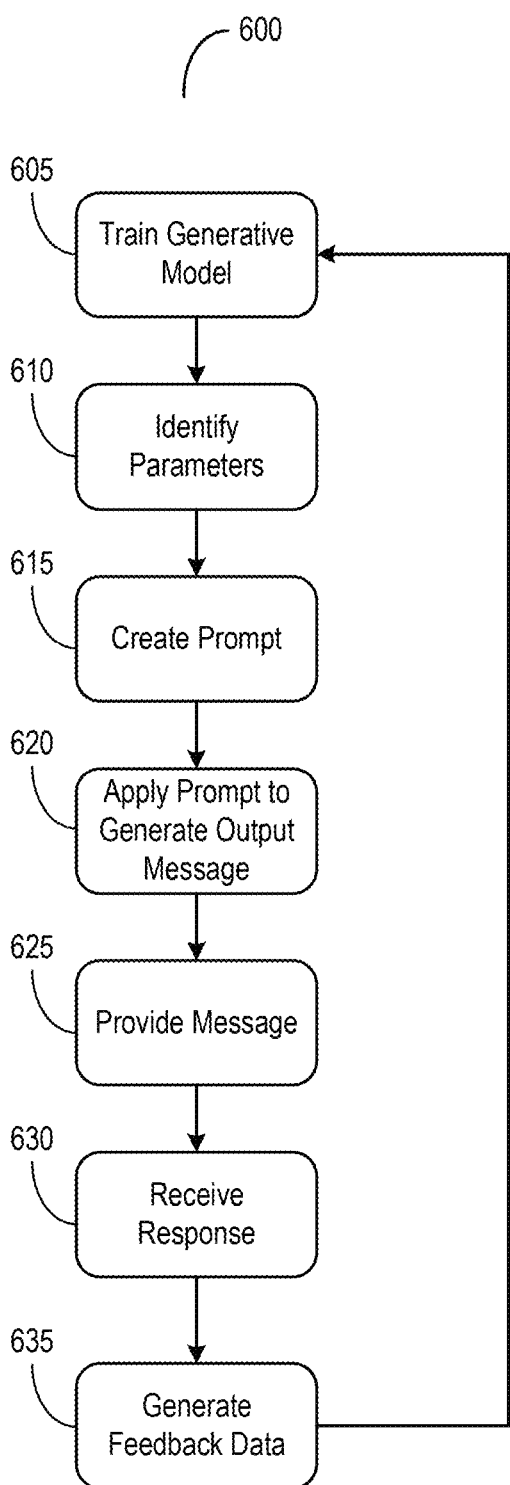
FIG. 6 depicts a flow diagram of a method of generating messages targeted at addressing conditions in users in accordance with an illustrative embodiment.

Referring now to FIG. 6, depicted is a method 600 for training a generative transformer model 165 based on the responses to a message transmitted to a user device 110. The method 600 can be implemented or performed using any of the components detailed herein such as the session management service 105, the user device 110, and the database 135, among others. Under method 600, a computing system (e.g., the session management system 105 or the user device 110 or both) may train a generative model (e.g., the generative transformer model 165) (605). The computing system may identify parameters (610). The computing system may create a prompt (e.g., the prompt 305) in accordance with a template (e.g., the template 185) (615). The computing system may apply the prompt to a generative model (e.g., the generative transformer model 165) generate an output message (e.g., the message 175') (620). The computing system may provide the output message to a user device (e.g., the user device 110) via an application (e.g., the application 120) (625). The message may be displayed on a user interface (e.g., the user interface 125) using user interface elements (e.g., the UI elements 130). The computing system may receive a response (e.g., the response 415) from a user (e.g., the user 405) through an interaction (e.g., the interaction 410) with the application on a user device (630). The computing system may generate feedback data (e.g., the feedback data 505) using the response (635). The computing system may use the feedback data to train the generative model and repeat the functionality from step (605).

B. Network and Computing Environment

Figure 7:
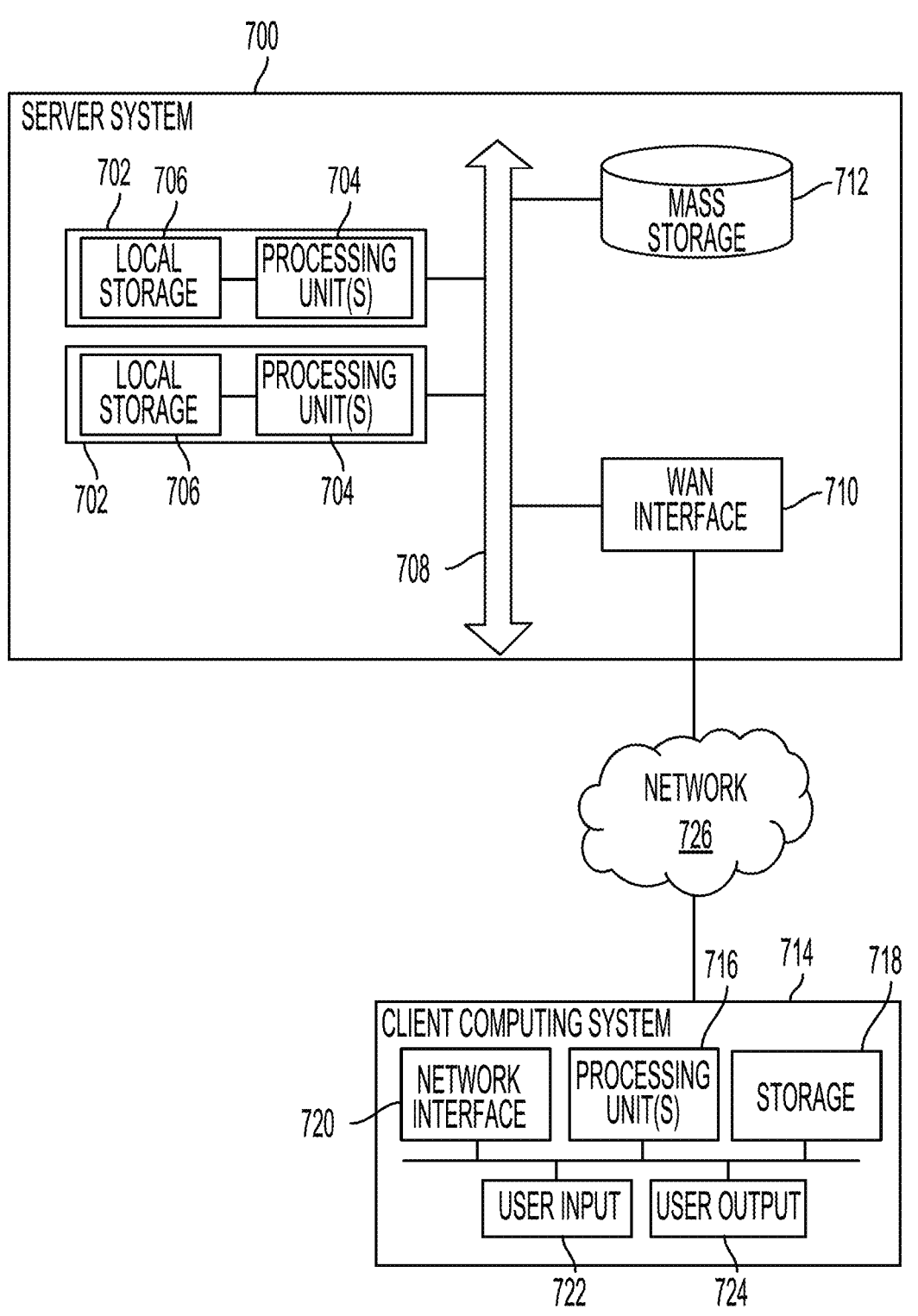
FIG. 7 is a block diagram of a server system and a client computer system in accordance with an illustrative embodiment.

Various operations described herein can be implemented on computer systems. FIG. 7 shows a simplified block diagram of a representative server system 700, client computer system 714, and network 726 usable to implement certain embodiments of the present disclosure. In various embodiments, server system 700 or similar systems can implement services or servers described herein or portions thereof. Client computer system 714 or similar systems can implement clients described herein. The system 100 described herein can be like the server system 700. Server system 700 can have a modular design that incorporates a number of modules 702 (e.g., blades in a blade server embodiment); while two modules 702 are shown, any number can be provided. Each module 702 can include processing unit(s) 704 and local storage 706.

Processing unit(s) 704 can include a single processor, which can have one or more cores, or multiple processors. In some embodiments, processing unit(s) 704 can include a general-purpose primary processor as well as one or more special-purpose co-processors, such as graphics processors, digital signal processors, or the like. In some embodiments, some or all processing units 704 can be implemented using customized circuits, such as application specific integrated circuits (ASICs) or field programmable gate arrays (FPGAs). In some embodiments, such integrated circuits execute instructions that are stored on the circuit itself. In other embodiments, processing unit(s) 704 can execute instructions stored in local storage 706. Any type of processors in any combination can be included in processing unit(s) 704.

Local storage 706 can include volatile storage media (e.g., DRAM, SRAM, SDRAM, or the like) and/or non-volatile storage media (e.g., magnetic, or optical disk, flash memory, or the like). Storage media incorporated in local storage 706 can be fixed, removable, or upgradeable as desired. Local storage 706 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 704 need at runtime. The ROM can store static data and instructions that are needed by processing unit(s) 704. The permanent storage device can be a non-volatile read-and-write memory device that can store instructions and data even when module 702 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 706 can store one or more software programs to be executed by processing unit(s) 704, such as an operating system and/or programs implementing various server functions such as functions of the system 100 or any other system described herein, or any other server(s) associated with system 100 or any other system described herein.

"Software" refers generally to sequences of instructions that, when executed by processing unit(s) 704, cause server system 700 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 704. Software can be implemented as a single program or a collection of separate programs or program modules that interact as desired. From local storage 706 (or non-local storage described below), processing unit(s) 704 can retrieve program instructions to execute and data to process to execute various operations described above.

In some server systems 700, multiple modules 702 can be interconnected via a bus or other interconnect 708, forming a local area network that supports communication between modules 702 and other components of server system 700. Interconnect 708 can be implemented using various technologies, including server racks, hubs, routers, etc.

A wide area network (WAN) interface 710 can provide data communication capability between the local area network (e.g., through the interconnect 708) and the network 726, such as the Internet. Other technologies can be used to communicatively couple the server system with the network 726, including wired (e.g., Ethernet, IEEE 802.3 standards) and/or wireless technologies (e.g., Wi-Fi, IEEE 802.11 standards).

In some embodiments, local storage 706 is intended to provide working memory for processing unit(s) 704, providing fast access to programs and/or data to be processed while reducing traffic on interconnect 708. Storage for larger quantities of data can be provided on the local area network by one or more mass storage subsystems 712 that can be connected to interconnect 708. Mass storage subsystem 712 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 712. In some embodiments, additional data storage resources may be accessible via WAN interface 710 (potentially with increased latency).

Server system 700 can operate in response to requests received via WAN interface 710. For example, one of modules 702 can implement a supervisory function and assign discrete tasks to other modules 702 in response to received requests. Work allocation techniques can be used. As requests are processed, results can be returned to the requester via WAN interface 710. Such operation can generally be automated. Further, in some embodiments, WAN interface 710 can connect multiple server systems 700 to each other, providing scalable systems capable of managing high volumes of activity. Other techniques for managing server systems and server farms (collections of server systems that cooperate) can be used, including dynamic resource allocation and reallocation.

Server system 700 can interact with various user-owned or user-operated devices via a wide-area network such as the Internet. An example of a user-operated device is shown in FIG. 7 as client computing system 714. Client computing system 714 can be implemented, for example, as a consumer device such as a smartphone, other mobile phone, tablet computer, wearable computing device (e.g., smart watch, eyeglasses), desktop computer, laptop computer, and so on. For example, client computing system 714 can communicate via WAN interface 720. Client computing system 714 can include computer components such as processing unit(s) 716, storage device 718, network interface 720, user input device 722, and user output device 724. Client computing system 714 can be a computing device implemented in a variety of form factors, such as a desktop computer, laptop computer, tablet computer, smartphone, other mobile computing device, wearable computing device, or the like.

Processing unit 716 and storage device 718 can be similar to processing unit(s) 704 and local storage 706 described above. Suitable devices can be selected based on the demands to be placed on client computing system 714; for example, client computing system 714 can be implemented as a "thin" client with limited processing capability or as a high-powered computing device. Client computing system 714 can be provisioned with program code executable by processing unit(s) 716 to enable various interactions with server system 700.

Network interface 720 can provide a connection to the network 726, such as a wide area network (e.g., the Internet) to which WAN interface 710 of server system 700 is also connected. In various embodiments, network interface 720 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 722 can include any device (or devices) via which a user can provide signals to client computing system 714; client computing system 714 can interpret the signals as indicative of user requests or information. In various embodiments, user input device 722 can include at least one of a keyboard, touch pad, touch screen, mouse, or other pointing device, scroll wheel, click wheel, dial, button, switch, keypad, microphone, and so on.

User output device 724 can include any device via which client computing system 714 can provide information to a user. For example, user output device 724 can include display-to-display images generated by or delivered to client computing system 714. The display can incorporate various image generation technologies, e.g., a liquid crystal display (LCD), light-emitting diode (LED) display including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 724 can be provided in addition to or instead of a display. Examples include indicator lights, speakers, tactile "display" devices, printers, and so on.

Some embodiments include electronic components, such as microprocessors, storage, and memory that store computer program instructions in a computer readable storage medium. Many of the features described in this specification can be implemented as processes that are specified as a set of program instructions encoded on a computer readable storage medium. When one or more processing units execute these program instructions, they cause the processing unit(s) to perform various operations indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 704 and 716 can provide various functionality for server system 700 and client computing system 714, including any of the functionality described herein as being performed by a server or client, or other functionality.

It will be appreciated that server system 700 and client computing system 714 are illustrative and that variations and modifications are possible. Computer systems used in connection with embodiments of the present disclosure can have other capabilities not specifically described here. Further, while server system 700 and client computing system 714 are described with reference to particular blocks, it is to be understood that these blocks are defined for convenience of description and are not intended to imply a particular physical arrangement of component parts. For instance, different blocks can be but need not be in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

While the disclosure has been described with respect to specific embodiments, one skilled in the art will recognize that numerous modifications are possible. Embodiments of the disclosure can be realized using a variety of computer systems and communication technologies, including but not limited to specific examples described herein. Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may refer to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or digital versatile disk (DVD), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

What is claimed is:

1. A method, comprising:

identifying, by one or more processors, (i) a condition of a user to be addressed and (ii) one or more parameters defining content to be presented via an application;

generating, by the one or more processors, an input based on the condition and the one or more parameters, in accordance with a template;

providing, by the one or more processors, the input to a generative model, wherein the generative model is trained by:

providing a set of inputs to the generative model to generate a set of outputs; and updating, using back propagation or an optimization function, the generative model based at least on the set of inputs and the set of outputs;

generating, by the one or more processors, based on providing the input to the generative model, content associated with addressing the condition of the user, wherein the content is generated based at least on a probability of engagement with the content by the user and comprises (i) a lesson comprising one or more explanations, instructions, or education materials for the user to view or read, the lesson selected for addressing the condition of the user, or (ii) one or more interactive elements configured to receive an input from the user indicating performance of an activity for addressing the condition of the user, the input provided via a user interface of the application; and providing, by the one or more processors, for presentation via the application, the content associated with addressing the condition of the user.

2. The method of claim 1, further comprising:

receiving, by the one or more processors, a response identifying interaction by a user via the application in response to the presentation of the content;

determining, by the one or more processors, based on the response, one or more second parameters to define content to be presented for the user;

generating, by the one or more processors, a second input based on the one or more second parameters, in accordance with the template;

providing, by the one or more processors, the second input to the generative model to generate second content associated with addressing the condition; and providing, by the one or more processors, for presentation via the application, the second content associated with addressing the condition.

3. The method of claim 1, further comprising:

receiving, by the one or more processors, a response identifying interaction by a user via the application in response to the presentation of the content; and updating, by the one or more processors, generation of content by the generative model using the response.

4. The method of claim 1, further comprising selecting, by the one or more processors, the template from a plurality of templates based on the condition to be addressed, the template including at least one placeholder to include at least one of the one or more parameters.

5. The method of claim 1, further comprising determining, by the one or more processors, a time at which to present the content to a user via the application, based on information associated with the user of the application.

6. The method of claim 1, wherein identifying the one or more parameters further comprises identifying, by the one or more processors, information on a user, to which content are to be presented, to use as at least one of the one or more parameters.

7. The method of claim 1, wherein identifying the one or more parameters further comprises selecting, by the one or more processors, a rule from a plurality of rules based on information on a user associated with the condition, to use as at least one of the one or more parameters.

8. The method of claim 1, wherein identifying the one or more parameters further comprises selecting, by the one or more processors, a plurality of candidate content based on an endpoint to be achieved towards addressing the condition, to use as at least one of the one or more parameters.

9. The method of claim 1, wherein generating the set of outputs further comprises selecting, by the one or more processors, at least one token to include in the set of outputs based on a probability of occurrence generated by the generative model for the at least one token.

10. The method of claim 1, wherein the generative model is established using a set of rules defining selection from a plurality of candidate content based on at least one of: (i) user behavior, (ii) user preference, or (iii) user profile information.

11. The method of claim 1, wherein the generative model is established using a plurality of corpora, at least a portion of the plurality of corpora comprising information associated with the condition to be addressed.

12. The method of claim 1, wherein a user is on a medication to address the condition, in partial concurrence with a session in which the content is provided, and wherein the content includes at least one of a short messaging service (SMS) message, a multimedia messaging service (MMS) message, or an in-app message.

13. A system, comprising:
one or more processors coupled with memory, configured to:
  identify (i) a condition in a user to be addressed and (ii) one or more parameters defining content to be presented via an application;
  generate an input based on the condition and the one or more parameters, in accordance with a template;
  provide the input to a generative model, wherein the generative model is trained by:
    providing a set of inputs to the generative model to generate a set of outputs; and
    updating, using back propagation or an optimization function, the generative model based at least on the set of inputs and the set of outputs;
  generate, based on providing the input to the generative model, content associated with addressing the condition of a user, wherein the content is generated based at least on a probability of engagement with the content by the user and comprises (i) a lesson comprising one or more explanations, instructions, or education materials for the user to view or read, the lesson selected for addressing the condition of the user, or (ii) one or more interactive elements configured to receive an input from the user indicating performance of an activity for addressing the condition of the user, the input provided via a user interface of the application; and provide, for presentation via the application, the content associated with addressing the condition of the user.

14. The system of claim 13, wherein the one or more processors are further configured to:
  receive a response identifying interaction by a user with the application in response to the presentation of the content;
  determine based on the response, one or more second parameters to define content to be presented for the user;
  generate a second input based on the one or more second parameters, in accordance with the template;
  provide the second input to the generative model to generate second content associated with addressing the condition; and
  provide, for presentation via the application, the second content associated with addressing the condition.

15. The system of claim 13, wherein the one or more processors are further configured to:
  receive a response identifying interaction by a user with the application in response to the presentation of the content; and
  update generation of content by the generative model using the response.

16. The system of claim 13, wherein the one or more processors are further configured to select the template from a plurality of templates based on the condition to be addressed, the template including at least one placeholder to include at least one of the one or more parameters.

17. The system of claim 13, wherein the one or more processors are further configured to determine a time at which to present the content to a user via the application, based on information associated with the user of the application.

18. The system of claim 13, wherein the one or more processors are further configured to identify information on a user, to which content are to be presented, to use as at least one of the one or more parameters.

19. The system of claim 13, wherein the one or more processors are further configured to select a rule from a plurality of rules based on information on a user associated with the condition, to use as at least one of the one or more parameters.

20. The system of claim 13, wherein the one or more processors are further configured to select a plurality of candidate content based on an endpoint to be achieved towards addressing the condition, to use as at least one of the one or more parameters.

21. The system of claim 13, wherein the one or more processors are further configured to select at least one token to include in the set of outputs based on a probability of occurrence generated by the generative model for the at least one token.

22. The system of claim 13, wherein the generative model is established using a set of rules defining selection from a plurality of candidate content based on at least one of: (i) user behavior, (ii) user preference, or (iii) user profile information.

23. The system of claim 13, wherein the generative model is established using a plurality of corpora, at least a portion of the plurality of corpora comprising information associated with the condition to be addressed.

24. The system of claim 13, wherein a user is on a medication to address the condition, in partial concurrence with a session in which the content is provided, and wherein the content includes at least one of a short messaging service (SMS) message, a multimedia messaging service (MMS) message, or an in-app message.

* * * * *